(12) United States Patent
Shi et al.

(10) Patent No.: US 11,261,478 B2
(45) Date of Patent: Mar. 1, 2022

(54) THERMAL STABLE LUCIFERASE WITH IMPROVED RESISTANCE TO INHIBITION BY LUCIFERIN BREAK-DOWN PRODUCTS

(71) Applicant: Promega Corporation, Madison, WI (US)

(72) Inventors: Ce Shi, Madison, WI (US); Thomas Kirkland, Atascadero, CA (US); Poncho Meisenheimer, San Luis Obispo, CA (US); Lance P. Encell, Fitchburg, WI (US); Mary Hall, Waunakee, WI (US)

(73) Assignee: Promega Corporation, Madison, WI (US)

( * ) Notice: Subject to any disclaimer, the term of this patent is extended or adjusted under 35 U.S.C. 154(b) by 115 days.

(21) Appl. No.: 16/335,638

(22) PCT Filed: Oct. 13, 2017

(86) PCT No.: PCT/US2017/056571
§ 371 (c)(1),
(2) Date: Mar. 21, 2019

(87) PCT Pub. No.: WO2018/071807
PCT Pub. Date: Apr. 19, 2018

(65) Prior Publication Data
US 2019/0309342 A1    Oct. 10, 2019

Related U.S. Application Data

(60) Provisional application No. 62/407,815, filed on Oct. 13, 2016.

(51) Int. Cl.
*C12Q 1/66* (2006.01)
*C12Q 1/00* (2006.01)
*C12N 9/02* (2006.01)

(52) U.S. Cl.
CPC .............. *C12Q 1/66* (2013.01); *C12N 9/0069* (2013.01); *C12Q 1/008* (2013.01); *C12Y 113/12007* (2013.01)

(58) Field of Classification Search
None
See application file for complete search history.

(56) References Cited

U.S. PATENT DOCUMENTS

| | | | | |
|---|---|---|---|---|
| 6,265,177 B1 * | 7/2001 | Squirrell | ............ | C12N 9/0069 435/189 |
| 6,602,677 B1 * | 8/2003 | Wood | .................... | C12N 9/0069 435/189 |
| 2005/0079567 A1 | 4/2005 | Choi et al. | | |
| 2006/0246529 A1 | 11/2006 | Yuan | | |
| 2009/0081680 A1 | 3/2009 | Tsunoda et al. | | |
| 2009/0286299 A1 | 11/2009 | Ronaghi et al. | | |
| 2010/0092966 A1 | 4/2010 | Burkhardt et al. | | |
| 2014/0170686 A1 * | 6/2014 | Squirrell | .............. | C12N 9/0069 435/8 |
| 2014/0201855 A1 * | 7/2014 | Miller | ...................... | C12Q 1/66 800/14 |
| 2014/0298500 A1 | 10/2014 | Binkowski et al. | | |
| 2016/0010143 A1 | 1/2016 | Burkhardt et al. | | |
| 2016/0291000 A1 | 10/2016 | Filipe et al. | | |

FOREIGN PATENT DOCUMENTS

| | | |
|---|---|---|
| EP | 1041151 | 10/2000 |
| EP | 1630231 | 3/2006 |
| EP | 2221386 | 8/2010 |
| WO | WO 1995/18853 | 7/1995 |

OTHER PUBLICATIONS

Branchini et al., Site-Directed Mutagenesis of Histidine 245 in Firefly Luciferase: A Proposed Model of the Active Site, Biochemistry 37, 1998, 15311-19. (Year: 1998).*
Conti et al., Crystal structure of firefly luciferase throws light on a superfamily of adenylate-forming enzymes, Structure 4, 1996, 287-98. (Year: 1996).*
Uniprot, Accession No. Q27757, 2015, www.uniprot.org. (Year: 2015).*
Branchini et al., Site-Directed Mutagenesis of Firefly Luciferase Active Site Amino Acids: A Proposed Model for Bioluminescence Color, Biochemistry 28, 1999, 13223-30. (Year: 1999).*
Fontes et al., Synthesis of Dehydroluciferin by Firefly Luciferase, Biochem. Biophys. Res. Comm. 237, 1997, 445-50. (Year: 1997).*
Endo et al., Advanced Bioluminescence System for In Vivo Imaging with Brighter and Red-Shifted Light Emission, Int. J. Mol. Sci. 21, 2020, 6538. (Year: 2020).*
Branchini et al., Red- and green-emitting firefly luciferase mutants for bioluminescent reporter applications, Analytical Biochem. 345, 2005, 140-48. (Year: 2005).*
Hall et al., Stabilization of firefly luciferase using directed evolution, Proceedings of the 10th international symposium on bioluminescence and chemiluminescence, 1998, John Wiley & Sons Ltd., pp. 392-395. (Year: 1998).*
Auld et al., A basis for reduced chemical library inhibition of firefly luciferase obtained from directed evolution. J Med Chem. Mar. 12, 2009;52(5):1450-8.
International Search Report and Written Opinion for PCT/US2017/056571, dated Mar. 28, 2018, 20 pages.
Extended EP Search Report for EP 17860669.5, dated Jul. 3, 2020, 10 pages.

* cited by examiner

*Primary Examiner* — Robert B Mondesi
*Assistant Examiner* — Todd M Epstein
(74) *Attorney, Agent, or Firm* — Casimir Jones SC; David W. Staple

(57) ABSTRACT

Provided herein are inhibitor-resistant luciferase mutants, and methods of use thereof. In particular, luciferase mutants are provided that are thermal stable and exhibit improved stability in the presence of luciferin break-down products, such as dehydroluciferin. Further provided are assay systems comprising inhibitor-resistant luciferase mutants and amino acid sequences of the inhibitor-resistant luciferase mutants.

19 Claims, 5 Drawing Sheets
Specification includes a Sequence Listing.

E6=H244R+C300G+I396K

B7=I240L+YY254S+C300G+T344A+I396K

E6=H244R+C300G+I396K

B7=I240L+YY254S+C300G+T344A+I396K

SEQUENCE LISTING

<160> NUMBER OF SEQ ID NOS: 12

<210> SEQ ID NO 1
<211> LENGTH: 550
<212> TYPE: PRT
<213> ORGANISM: Photinus pyralis

<400> SEQUENCE: 1

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255
```

Ile Cys Gly Phe Arg Val Val Leu Met Tyr Arg Glu Glu Leu
              260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
    435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 2
<211> LENGTH: 2387
<212> TYPE: DNA
<213> ORGANISM: Photinus pyralis

<400> SEQUENCE: 2
ctgcagaaat aactaggtac taagcccgtt tgtgaaaagt ggccaaaccc ataaatttgg    60
caattacaat aaagaagcta aaattgtggt caaactcaca acatttttta ttatatacat    120
tttagtagct gatgcttata aaagcaatat ttaaatcgta acaacaaat aaaataaaat    180 ttaaacgatg tgattaagag ccaaaggtcc tctagaaaaa ggtatttaag caacggaatt    240
cctttgtgtt acattcttga atgtcgctcg cagtgacatt agcattccgg tactgttggt    300
aaaatggaag acgccaaaaa cataaagaaa ggcccggcgc cattctatcc tctagaggat    360
ggaaccgctg gagagcaact gcataaggct atgaagagat acgccctggt tcctggaaca    420

```
attgcttttg tgagtatttc tgtctgattt ctttcgagtt aacgaaatgt tcttatgttt    480 cttagacag atgcacatat cgaggtgaac atcacgtacg cggaatactt cgaaatgtcc    540
gttcggttgg cagaagctat gaaacgatat gggctgaata caaatcacag aatcgtcgta   600
tgcagtgaaa actctcttca attctttatg ccggtgttgg gcgcgttatt tatcggagtt   660
gcagttgcgc ccgcgaacga catttataat gaacgtaagc accctcgcca tcagaccaaa   720
gggaatgacg tatttaattt ttaaggtgaa ttgctcaaca gtatgaacat ttcgcagcct   780
accgtagtgt ttgtttccaa aaagggggttg caaaaaattt tgaacgtgca aaaaaaatta   840
ccaataatcc agaaaattat tatcatggat tctaaaacgg attaccaggg atttcagtcg   900
atgtacacgt tcgtcacatc tcatctacct cccggtttta atgaatacga ttttgtacca   960
gagtcctttg atcgtgacaa aacaattgca ctgataatga attcctctgg atctactggg   1020
ttacctaagg gtgtggccct tccgcataga actgcctgcg tcagattctc gcatgccagg   1080
tatgtcgtat aacaagagat taagtaatgt tgctacacac attgtagaga tcctattttt   1140
ggcaatcaaa tcattccgga tactgcgatt ttaagtgttg ttccattcca tcacggtttt   1200
ggaatgttta ctacactcgg atatttgata tgtggatttc gagtcgtctt aatgtataga   1260
tttgaagaag agctgttttt acgatccctt caggattaca aaattcaaag tgcgttgcta   1320
gtaccaaccc tattttcatt cttcgccaaa agcactctga ttgacaaata cgatttatct   1380
aatttacacg aaattgcttc tggggggcgca cctctttcga agaagtcgg ggaagcggtt   1440 gcaaaacggt gagttaagcg cattgctagt atttcaaggc tctaaaacgg cgcgtagctt   1500
ccatcttcca gggatacgac aaggatatgg gctcactgag actacatcag ctattctgat   1560
tacacccgag ggggatgata aaccgggcgc ggtcggtaaa gttgttccat tttttgaagc   1620
gaaggttgtg gatctggata ccgggaaaac gctgggcgtt aatcagagag gcgaattatg   1680
tgtcagagga cctatgatta tgtccggtta tgtaaacaat ccggaagcga ccaacgcctt   1740
gattgacaag gatggatggc tacattctgg agacatagct tactgggacg aagacgaaca   1800
cttcttcata gttgaccgct tgaagtcttt aattaaatac aaaggatatc aggtaatgaa   1860 gattttaca tgcacacacg ctacaatacc tgtaggtggc ccccgctgaa ttggaatcga   1920
tattgttaca acaccccaac atcttcgacg cgggcgtggc aggtcttccc gacgatgacg   1980
ccggtgaact tcccgccgcc gttgttgttt tggagcacgg aaagacgatg acggaaaaag   2040
agatcgtgga ttacgtcgcc agtaaatgaa ttcgttttac gttactcgta ctacaattct   2100
tttcataggt caagtaacaa ccgcgaaaaa gttgcgcgga ggagttgtgt ttgtggacga   2160
agtaccgaaa ggtcttaccg gaaaactcga cgcaagaaaa atcagagaga tcctcataaa   2220
ggccaagaag ggcggaaagt ccaaattgta aaatgtaact gtattcagcg atgacgaaat   2280
tcttagctat tgtaatatta tatgcaaatt gatgaatggt aattttgtaa ttgtgggtca   2340
ctgtactatt ttaacgaata ataaaatcag gtataggtaa ctaaaaa                 2387
```

<210> SEQ ID NO 3
<211> LENGTH: 552
<212> TYPE: PRT
<213> ORGANISM: Artificial sequence
<220> FEATURE:
<223> OTHER INFORMATION: Synthetic

<400> SEQUENCE: 3

Met Ala Asp Lys Asn Ile Leu Tyr Gly Pro Glu Pro Phe Tyr Pro Leu
1               5                   10                  15

```
Glu Asp Gly Thr Ala Gly Glu Gln Met Phe Asp Ala Leu Ser Arg Tyr
         20                  25                  30

Ala Ala Ile Pro Gly Cys Ile Ala Leu Thr Asn Ala His Thr Lys Glu
             35                  40                  45

Asn Val Leu Tyr Glu Glu Phe Leu Lys Leu Ser Cys Arg Leu Ala Glu
 50                  55                  60

Ser Phe Lys Lys Tyr Gly Leu Lys Gln Asn Asp Thr Ile Ala Val Cys
 65                  70                  75                  80

Ser Glu Asn Ser Leu Gln Phe Phe Leu Pro Val Ile Ala Ser Leu Tyr
                 85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
            115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
            195                 200                 205

Leu Thr His Lys Asn Ile Val Ala Arg Phe Ser Ile Ala Lys Asp Pro
            210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
            275                 280                 285

Thr Leu Met Ala Phe Leu Ala Lys Ser Ala Leu Cys Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Lys Pro Gly Ser Thr Gly Lys Ile Val Pro Leu His
            355                 360                 365

Ala Val Lys Val Val Asp Pro Thr Thr Gly Lys Ile Leu Gly Pro Asn
            370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430
```

Ile Val Asp Arg Leu Lys Ser Leu Ile Lys Tyr Lys Gly Tyr Gln Val
           435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Leu Glu Lys His Thr Asn Gly
    530                 535                 540

His His His His His His His His
545                 550

<210> SEQ ID NO 4
<211> LENGTH: 1659
<212> TYPE: DNA
<213> ORGANISM: Artificial sequence
<220> FEATURE:
<223> OTHER INFORMATION: Synthetic

<400> SEQUENCE: 4
atggctgaca aaacatcct gtatggtccg gaaccgttct acccactgga agatggtacc      60
gctggtgaac agatgtttga cgcattatct cgttatgcag ctattccggg ctgcatagca     120
ttgacaaatg ctcatacaaa agaaaatgtt ttatatgaag agtttctgaa actgtcgtgt     180
cgtttagcgg aaagttttaa aaagtatgga ttaaaacaaa acgacacaat agcggtgtgt     240
agcgaaaata gtctgcaatt tttccttcct gtaattgcat cattgtatct tggaataatt     300
gtggcacctg ttaacgataa atacattgaa cgtgaattaa tacacagtct tggtattgta     360
aaaccacgca tagtttttg ctccaagaat acttttcaaa aagtactgaa tgtaaaatct     420
aaattaaaat ctattgaaac tattattata ttagacttaa atgaagactt aggaggttat     480
caatgcctca acaactttat ttctcaaaat tccgatagta atctggacgt aaaaaaattt     540
aaacccctatt cttttaatcg agacgatcag gttgcgtcga ttatgttttc ttctggtaca     600
actggtctgc cgaagggagt catgctaact cacaagaata ttgttgcacg attttctatt     660
gcaaaagatc ctacttttgg taacgcaatt aatcccacgt cagcaatttt aacggtaata     720
cctttccacc atggttttgg tatgatgacc acattaggat actttacttg tggattccga     780
gttgttctaa tgcacacgtt tgaagaaaaa ctatttctac aatcattaca agattataaa     840
gtggaaagta ctttacttgt accaacatta atggcatttc ttgcaaaaag tgcattagtt     900
gaaaagtacg atttatcgca cttaaaagaa attgcatctg gtggcgcacc tttatcaaaa     960
gaaattgggg agatggtgaa aaaacggttt aaattaaact tgtcaggca agggtatgga    1020
ttaacagaaa ccacttcggc tgttttaatt acaccgaaag gtgacgccaa accgggatca    1080
actggtaaaa tagtaccatt acacgctgtt aaagttgtcg atcctacaac aggaaaaatt    1140
ttggggccaa atgaacctgg agaattgtat tttaaaggcc cgatgataat gaagggttat    1200
tataataatg aagaagctac taaagcaatt attgataatg acggatggtt gcgctctggt    1260
gatattgctt attatgacaa tgatggccat ttttatattg tggacaggct gaagtcactg    1320
attaaatata aaggttatca ggttgcacct gctgaaattg agggaatact cttacaacat    1380

```
ccgtatattg ttgatgccgg cgttactggt ataccggatg aagccgcggg cgagcttcca    1440
gctgcaggtg ttgtagtaca gactggaaaa tatctaaacg aacaaatcgt acaagattat    1500
gttgccagtc aagtttcaac agccaaatgg ctacgtggtg gggtgaaatt tttggatgaa    1560
attcccaaag gatcaactgg aaaaattgac agaaaagtgt taagacaaat gttagaaaaa    1620
cacaccaatg ggcatcacca tcaccaccat catcactaa                           1659
```

```
<210> SEQ ID NO 5
<211> LENGTH: 552
<212> TYPE: PRT
<213> ORGANISM: Artificial sequence
<220> FEATURE:
<223> OTHER INFORMATION: Synthetic

<400> SEQUENCE: 5
```

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Ala Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
    130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
        195                 200                 205

Leu Thr His Lys Asn Ile Val Ala Arg Phe Ser Ile Ala Lys Asp Pro
    210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Gly Glu Lys Tyr Asp
    290                 295                 300

Leu Ser His Leu Lys Glu Ile Ala Ser Gly Gly Ala Pro Leu Ser Lys

```
            305                 310                 315                 320
Glu Ile Gly Glu Met Val Lys Lys Arg Phe Lys Leu Asn Phe Val Arg
                325                 330                 335
Gln Gly Tyr Gly Leu Thr Glu Thr Thr Ser Ala Val Leu Ile Thr Pro
                340                 345                 350
Lys Gly Asp Ala Lys Pro Gly Ser Thr Gly Lys Ile Val Pro Leu His
                355                 360                 365
Ala Val Lys Val Val Asp Pro Thr Thr Gly Lys Ile Leu Gly Pro Asn
            370                 375                 380
Glu Pro Gly Glu Leu Tyr Phe Lys Gly Pro Met Lys Met Lys Gly Tyr
385                 390                 395                 400
Tyr Asn Asn Glu Glu Ala Thr Lys Ala Ile Ile Asp Asn Asp Gly Trp
                    405                 410                 415
Leu Arg Ser Gly Asp Ile Ala Tyr Tyr Asp Asn Asp Gly His Phe Tyr
                420                 425                 430
Ile Val Asp Arg Leu Lys Ser Leu Ile Lys Tyr Lys Gly Tyr Gln Val
                435                 440                 445
Ala Pro Ala Glu Ile Glu Gly Ile Leu Leu Gln His Pro Tyr Ile Val
            450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asp Tyr Val Ala Ser Gln Val Ser Thr Ala Lys Trp Leu Arg
                500                 505                 510
Gly Gly Val Lys Phe Leu Asp Glu Ile Pro Lys Gly Ser Thr Gly Lys
            515                 520                 525
Ile Asp Arg Lys Val Leu Arg Gln Met Leu Glu Lys His Thr Asn Gly
            530                 535                 540
His His His His His His His
545                 550

<210> SEQ ID NO 6
<211> LENGTH: 1660
<212> TYPE: DNA
<213> ORGANISM: Artificial sequence
<220> FEATURE:
<223> OTHER INFORMATION: Synthetic

<400> SEQUENCE: 6
atggctgaca aaacatcct gtatggtccg gaaccgttct acccactgga agatggtacc      60
gctggtgaac agatgtttga cgcattatct cgttatgcag ctattccggg ctgcatagca     120
ttgacaaatg ctcatacaaa agaaatgtt ttatatgaag agtttctgaa actgtcgtgt     180
cgtttagcgg aaagttttaa aaagtatgga ttaaaacaaa atgacacaat agcggtgtgt     240
agcgaaaata gtctgcaatt tttccttcct gtaattgcat cattgtatct tggaataatt     300
gtggcacctg ttaacgataa atacattgaa cgtgaattaa tacacagtct tggtattgta     360
aaaccacgca tagttttttg ctccaagaat acttttcaaa agtactgaa tgtaaaatct     420 aaattaaaat ctattgaaac tattattata ttagactaa atgaagactt aggaggttat     480
caatgcctca acaactttat ttctcaaaat tccgatagta atctggacgt aaaaaaattt     540
aaaccctatt cttttaatcg agacgatcag gttgcgtcga ttatgttttc ttctggtaca     600
actggtctgc cgaagggagt catgctaact cacaagaata ttgttgcacg atttctatt     660
```

```
gcaaaagatc ctactttggg taacgcaatt aatcccacgt cagcaatttt aacggtaata      720
cctttccacc gtggttttgg tatgatgacc acattaggat actttacttg tggattccga      780
gttgttctaa tgcacacgtt tgaagaaaaa ctatttctac aatcattaca agattataaa      840
gtggaaagta ctttacttgt accaacatta atggcatttc ttgcaaaaag tgcattaggt      900
gaaaagtacg atttatcgca cttaaaagaa attgcatctg gtggcgcacc tttatcaaaa      960
gaaattgggg agatggtgaa aaacggtttt aaattaaact tgtcaggca agggtatgga     1020 ttaacagaaa ccacttcggc tgttttaatt acaccgaaag gtgacgccaa accgggatca     1080
actggtaaaa tagtaccatt acacgctgtt aaagttgtcg atcctacaac aggaaaaatt     1140
ttggggccaa atgaacctgg agaattgtat tttaaaggcc cgatgaaaat gaagggttat     1200
tataataatg aagaagctac taaagcaatt attgataatg acggatggtt gcgctctggt     1260
gatattgctt attatgacaa tgatggccat ttttatattg tggacaggct gaagtcactg     1320
attaaatata aaggttatca ggttgcacct gctgaaattg agggaatact cttacaacat     1380
ccgtatattg ttgatgccgg cgttactggt ataccggatg aagccgcggg cgagcttcca     1440
gctgcaggtg ttgtagtaca gactggaaaa tatctaaacg aacaaatcgt acaagattat     1500
gttgccagtc aagtttcaac agccaaatgg ctacgtggtg gggtgaaatt tttggatgaa     1560
attcccaaag gatcaactgg aaaaattgac agaaaagtgt taagacaaat gttagaaaaa     1620
cacaccaatg gcatcacca tcaccaccat catcactaat                            1660
```

<210> SEQ ID NO 7
<211> LENGTH: 552
<212> TYPE: PRT
<213> ORGANISM: Artificial sequence
<220> FEATURE:
<223> OTHER INFORMATION: Synthetic

<400> SEQUENCE: 7

```
Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Ala Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
    130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190
```

```
Ser Ile Met Phe Ser Ser Gly Thr Thr Gly Leu Pro Lys Gly Val Met
            195                 200                 205
Leu Thr His Lys Asn Ile Val Ala Arg Phe Ser Ile Ala Lys Asp Pro
210                 215                 220
Thr Phe Gly Asn Ala Ile Asn Pro Thr Ser Ala Ile Leu Thr Val Leu
225                 230                 235                 240
Pro Phe His His Gly Phe Gly Met Met Thr Thr Leu Gly Ser Phe Thr
                245                 250                 255
Cys Gly Phe Arg Val Val Leu Met His Thr Phe Glu Glu Lys Leu Phe
                260                 265                 270
Leu Gln Ser Leu Gln Asp Tyr Lys Val Glu Ser Thr Leu Leu Val Pro
            275                 280                 285
Thr Leu Met Ala Phe Leu Ala Lys Ser Ala Leu Val Glu Lys Tyr Asp
290                 295                 300
Leu Ser His Leu Lys Glu Ile Ala Ser Gly Gly Ala Pro Leu Ser Lys
305                 310                 315                 320
Glu Ile Gly Glu Met Val Lys Lys Arg Phe Lys Leu Asn Phe Val Arg
                325                 330                 335
Gln Gly Tyr Gly Leu Thr Glu Ala Thr Ser Ala Val Leu Ile Thr Pro
            340                 345                 350
Lys Gly Asp Ala Lys Pro Gly Ser Thr Gly Lys Ile Val Pro Leu His
355                 360                 365
Ala Val Lys Val Val Asp Pro Thr Thr Gly Lys Ile Leu Gly Pro Asn
370                 375                 380
Glu Pro Gly Glu Leu Tyr Phe Lys Gly Pro Met Lys Met Lys Gly Tyr
385                 390                 395                 400
Tyr Asn Asn Glu Glu Ala Thr Lys Ala Ile Ile Asp Asn Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
            435                 440                 445
Ala Pro Ala Glu Ile Glu Gly Ile Leu Leu Gln His Pro Tyr Ile Val
450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asp Tyr Val Ala Ser Gln Val Ser Thr Ala Lys Trp Leu Arg
            500                 505                 510
Gly Gly Val Lys Phe Leu Asp Glu Ile Pro Lys Gly Ser Thr Gly Lys
            515                 520                 525
Ile Asp Arg Lys Val Leu Arg Gln Met Leu Glu Lys His Thr Asn Gly
530                 535                 540
His His His His His His His
545                 550
```

<210> SEQ ID NO 8
<211> LENGTH: 1659
<212> TYPE: DNA
<213> ORGANISM: Artificial sequence
<220> FEATURE:
<223> OTHER INFORMATION: Synthetic

<400> SEQUENCE: 8

```
atggctgaca aaaacatcct gtatggtccg gaaccgttct acccactgga agatggtacc      60
gctggtgaac agatgtttga cgcattatct cgttatgcag ctattccggg ctgcatagca     120
ttgacaaatg ctcatacaaa agaaaatgtt ttatatgaag agtttctgaa actgtcgtgt     180
cgtttagcgg aaagttttaa aaagtatgga ttaaaacaaa acgacacaat agcggtgtgt     240
agcgaaaata gtctgcaatt tttccttcct gtaattgcat cattgtatct tggaataatt     300
gtggcacctg ttaacgataa atacattgaa cgtgaattaa tacacagtct tggtattgta     360
aaaccacgca tagttttttg ctccaagaat acttttcaaa aagtactgaa tgtaaaatct     420
aaattaaaat ctattgaaac tattattata ttagacttaa atgaagactt aggaggttat     480
caatgcctca acaactttat ttctcaaaat tccgatagta atctggacgt aaaaaaattt     540
aaaccctatt cttttaatcg agacgatcag gttgcgtcga ttatgttttc ttctggtaca     600
actggtctgc cgaagggagt catgctaact cacaagaata ttgttgcacg atttctatt      660
gcaaagatc ctactttttgg taacgcaatt aatcccacgt cagcaatttt aacggtatta     720
cctttccacc atggttttgg tatgatgacc acattaggat cctttacttg tggattccga     780
gttgttctaa tgcacacgtt tgaagaaaaa ctatttctac aatcattaca agattataaa     840
gtggaaagta ctttacttgt accaacatta atggcatttc ttgcaaaaag tgcattagtt     900
gaaaagtacg atttatcgca cttaaaagaa attgcatctg gtggcgcacc tttatcaaaa     960
gaaattgggg agatggtgaa aaaacggttt aaattaaact tgtcaggca agggtatgga    1020
ttaacagaag ccacttcggc tgttttaatt acaccgaaag gtgacgccaa accgggatca    1080
actggtaaaa tagtaccatt acacgctgtt aaagttgtcg atcctacaac aggaaaaatt    1140
tgggggccaa atgaacctgg agaattgtat tttaaaggcc cgatgaaaat gaagggttat    1200
tataataatg aagaagctac taaagcaatt attgataatg acggatggtt gcgctctggt    1260
gatattgctt attatgacaa tgatggccat ttttatattg tggacaggct gaagtcactg    1320
attaaatata aaggttatca ggttgcacct gctgaaattg agggaatact cttacaacat    1380
ccgtatattg ttgatgccgg cgttactggt ataccggatg aagccgcggg cgagcttcca    1440
gctgcaggtg ttgtagtaca gactggaaaa tatctaaacg aacaaatcgt acaagattat    1500
gttgccagtc aagtttcaac agccaaatgg ctacgtggtg gggtgaaatt tttggatgaa    1560
attcccaaag gatcaactgg aaaaattgac agaaaagtgt aagcaaat gttagaaaaa    1620
cacaccaatg ggcatcacca tcaccaccat catcactaa                           1659
```

<210> SEQ ID NO 9
<211> LENGTH: 552
<212> TYPE: PRT
<213> ORGANISM: Artificial sequence
<220> FEATURE:
<223> OTHER INFORMATION: Synthetic

<400> SEQUENCE: 9

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Ala Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

```
Ser Phe Lys Lys Tyr Gly Leu Lys Gln Asn Asp Thr Ile Ala Val Cys
 65                  70                  75                  80

Ser Glu Asn Ser Leu Gln Phe Phe Leu Pro Val Ile Ala Ser Leu Tyr
                 85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
            115                 120                 125

Lys Asn Thr Phe Gln Lys Val Leu Asn Val Lys Ser Lys Leu Lys Ser
        130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
        195                 200                 205

Leu Thr His Lys Asn Ile Val Ala Arg Phe Ser Ile Ala Lys Asp Pro
210                 215                 220

Thr Phe Gly Asn Ala Ile Asn Pro Thr Ser Ala Ile Leu Thr Val Ile
225                 230                 235                 240

Pro Phe His Trp Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Ala Thr Ser Ala Val Leu Ile Thr Pro
            340                 345                 350

Lys Gly Asp Ala Lys Pro Gly Ser Thr Gly Lys Ile Val Pro Leu His
        355                 360                 365

Ala Val Lys Val Val Asp Pro Thr Thr Gly Lys Ile Leu Gly Pro Asn
370                 375                 380

Glu Pro Gly Glu Leu Tyr Phe Lys Gly Pro Met Lys Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
        450                 455                 460

Asp Ala Gly Val Thr Gly Ile Pro Asp Glu Ala Ala Gly Glu Leu Pro
465                 470                 475                 480

Ala Ala Gly Val Val Val Gln Thr Gly Lys Tyr Leu Asn Glu Gln Ile
```

```
                485               490               495
Val Gln Asp Tyr Val Ala Ser Gln Val Ser Thr Ala Lys Trp Leu Arg
            500               505               510

Gly Gly Val Lys Phe Leu Asp Glu Ile Pro Lys Gly Ser Thr Gly Lys
        515               520               525

Ile Asp Arg Lys Val Leu Arg Gln Met Leu Glu Lys His Thr Asn Gly
    530               535               540

His His His His His His His
545               550
```

<210> SEQ ID NO 10
<211> LENGTH: 1659
<212> TYPE: DNA
<213> ORGANISM: Artificial sequence
<220> FEATURE:
<223> OTHER INFORMATION: Synthetic

<400> SEQUENCE: 10

```
atggctgaca aaacatcct gtatggtccg gaaccgttct acccactgga agatggtacc      60
gctggtgaac agatgtttga cgcattatct cgttatgcag ctattccggg ctgcatagca     120
ttgacaaatg ctcatacaaa agaaaatgtt ttatatgaag agtttctgaa actgtcgtgt     180
cgtttagcgg aaagttttaa aaagtatgga ttaaaacaaa acgacacaat agcggtgtgt     240
agcgaaaata gtctgcaatt tttccttcct gtaattgcat cattgtatct tggaataatt     300
gtggcacctg ttaacgataa atacattgaa cgtgaattaa tacacagtct tggtattgta     360
aaaccacgca tagtttttg ctccaagaat acttttcaaa aagtactgaa tgtaaaatct     420
aaattaaaat ctattgaaac tattattata ttagacttaa atgaagactt aggaggttat     480
caatgcctca acaactttat ttctcaaaat tccgatagta atctggacgt aaaaaaattt     540
aaaccctatt cttttaatcg agacgatcag gttgcgtcga ttatgttttc ttctggtaca     600
actggtctgc gaagggagt catgctaact cacaagaata ttgttgcacg attttctatt     660
gcaaaagatc ctactttggg taacgcaatt aatcccacgt cagcaatttt aacggtaata     720
cctttccact ggggttttgg tatgatgacc acattaggat actttacttg tggattccga     780
gttgttctaa tgcacacgtt tgaagaaaaa ctatttctac aatcattaca agattataaa     840
gtggaaagta ctttacttgt accaacatta atggcatttc ttgcaaaaag tgcattagtt     900
gaaaagtacg atttatcgca cttaaaagaa attgcatctg gtggcgcacc tttatcaaaa     960
gaaattgggg agatggtgaa aaaacggttt aaattaaact tgtcaggca agggtatgga    1020
ttaacagaag ccacttcggc tgttttaatt acaccgaaag gtgacgccaa accgggatca    1080
actggtaaaa tagtaccatt acacgctgtt aagttgtcg atcctacaac aggaaaaatt    1140
ttggggccaa atgaacctgg agaattgtat tttaaaggcc cgatgaaaat gaagggttat    1200
tataataatg aagaagctac taaagcaatt attgataatg acggatggtt gcgctctggt    1260
gatattgctt attatgacaa tgatggccat ttttatattg tggacaggct gaagtcactg    1320
attaaatata aaggttatca ggttgcacct gctgaaattg agggaatact cttacaacat    1380
ccgtatattg ttgatgccgg cgttactggt ataccggatg aagccgcggg cgagcttcca    1440
gctgcaggtg ttgtagtaca gactggaaaa tatctaaacg aacaaatcgt acaagattat    1500
gttgccagtc aagtttcaac agccaaatgg ctacgtggtg gggtgaaatt tttggatgaa    1560
attcccaaag gatcaactgg aaaaattgac agaaaagtgt taagacaaat gttagaaaaa    1620
cacaccaatg ggcatcacca tcaccaccat catcactaa                          1659
```

<210> SEQ ID NO 11
<211> LENGTH: 552
<212> TYPE: PRT
<213> ORGANISM: Artificial sequence
<220> FEATURE:
<223> OTHER INFORMATION: Synthetic

<400> SEQUENCE: 11

```
Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
                20                  25                  30

Ala Ala Ile Pro Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
        195                 200                 205

Leu Thr His Lys Asn Ile Val Ala Arg Phe Ser Ile Ala Lys Asp Pro
210                 215                 220

Thr Phe Gly Asn Ala Ile Asn Pro Thr Ser Ala Ile Leu Thr Val Ile
225                 230                 235                 240

Pro Phe His Trp Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Gly Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Ala Thr Ser Ala Val Leu Ile Thr Pro
            340                 345                 350

Lys Gly Asp Ala Lys Pro Gly Ser Thr Gly Lys Ile Val Pro Leu His
        355                 360                 365
```

Ala Val Lys Val Val Asp Pro Thr Thr Gly Lys Ile Leu Gly Pro Asn
            370                 375                 380

Glu Pro Gly Glu Leu Tyr Phe Lys Gly Pro Met Lys Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
        450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Leu Glu Lys His Thr Asn Gly
530                 535                 540

His His His His His His His His
545                 550

<210> SEQ ID NO 12
<211> LENGTH: 1659
<212> TYPE: DNA
<213> ORGANISM: Artificial sequence
<220> FEATURE:
<223> OTHER INFORMATION: Synthetic

<400> SEQUENCE: 12
atggctgaca aaaacatcct gtatggtccg gaaccgttct acccactgga agatggtacc      60
gctggtgaac agatgtttga cgcattatct cgttatgcag ctattccggg ctgcatagca     120
ttgacaaatg ctcatacaaa agaaaatgtt ttatatgaag agtttctgaa actgtcgtgt     180
cgtttagcgg aaagttttaa aaagtatgga ttaaaacaaa acgacacaat agcggtgtgt     240
agcgaaaata gtctgcaatt tttccttcct gtaattgcat cattgtatct tggaataatt     300
gtggcacctg ttaacgataa atacattgaa cgtgaattaa tacacagtct tggtattgta     360
aaaccacgca tagttttttg ctccaagaat acttttcaaa aagtactgaa tgtaaaatct     420
aaattaaaat ctattgaaac tattattata ttagacttaa atgaagactt aggaggttat     480
caatgcctca caactttat ttctcaaaat tccgatagta atctggacgt aaaaaaattt     540
aaaccctatt cttttaatcg agacgatcag gttgcgtcga ttatgttttc ttctggtaca     600
actggtctgc cgaagggagt catgctaact cacaagaata ttgttgcacg attttctatt     660 gcaaagatc ctactttttgg taacgcaatt aatcccacgt cagcaatttt aacggtaata     720
cctttccact ggggttttgg tatgatgacc acattaggat acttttacttg tggattccga     780 gttgttctaa tgcacacgtt tgaagaaaaa ctatttctac aatcattaca agattataaa     840
gtggaaagta ctttacttgt accaacatta atggcatttc ttgcaaaaag tgcattaggt     900
gaaaagtacg atttatcgca cttaaaagaa attgcatctg tggcgcacc tttatcaaaa     960

```
gaaattgggg agatggtgaa aaaacggttt aaattaaact ttgtcaggca agggtatgga    1020
ttaacagaag ccacttcggc tgttttaatt acaccgaaag gtgacgccaa accgggatca    1080
actggtaaaa tagtaccatt acacgctgtt aaagttgtcg atcctacaac aggaaaaatt    1140
ttggggccaa atgaacctgg agaattgtat tttaaaggcc cgatgaaaat gaagggttat    1200
tataataatg aagaagctac taaagcaatt attgataatg acggatggtt gcgctctggt    1260
gatattgctt attatgacaa tgatggccat ttttatattg tggacaggct gaagtcactg    1320
attaaatata aaggttatca ggttgcacct gctgaaattg agggaatact cttacaacat    1380
ccgtatattg ttgatgccgg cgttactggt ataccggatg aagccgcggg cgagcttcca    1440
gctgcaggtg ttgtagtaca gactggaaaa tatctaaacg aacaaatcgt acaagattat    1500
gttgccagtc aagtttcaac agccaaatgg ctacgtggtg gggtgaaatt tttggatgaa    1560
attcccaaag gatcaactgg aaaaattgac agaaaagtgt taagacaaat gttagaaaaa    1620
cacaccaatg ggcatcacca tcaccaccat catcactaa                          1659
```

THERMAL STABLE LUCIFERASE WITH IMPROVED RESISTANCE TO INHIBITION BY LUCIFERIN BREAK-DOWN PRODUCTS

CROSS-REFERENCE TO RELATED APPLICATION

The present application claims priority to U.S. Provisional Patent Application Ser. No. 62/407,815 filed Oct. 13, 2016, which is hereby incorporated by reference in its entirety.

SEQUENCE LISTING

The text of the computer readable sequence listing filed herewith, titled "34943-US-2-PCT ST25", created Mar. 21, 2019, having a file size of 43,749 bytes, is hereby incorporated by reference in its entirety.

FIELD

Provided herein are inhibitor-resistant luciferase mutants and methods of use thereof. In particular, luciferase mutants are provided that are thermal stable and exhibit improved resistance to inhibition by luciferin break-down products such as dehydroluciferin.

BACKGROUND

Quantitative detection of ATP is commonly performed using a luciferase enzyme (e.g., firefly luciferase) and its substrate (e.g., D-luciferin).

SUMMARY

Provided herein are inhibitor-resistant luciferase mutants and methods of use thereof. In particular, luciferase mutants are provided that are thermal stable and exhibit improved resistance to inhibition by luciferin break-down products such as dehydroluciferin.

The stability and reliability of ATP-detection assays and reagents is compromised in the presence of luciferin break-down products which inhibit luciferase and result in decreased light output. These breakdown products are particularly problematic when luciferin and luciferase are stored together as single liquid reagent, resulting in reduced shelf-life. Dehydroluciferin has been identified as the major inhibitory breakdown product of luciferin.

In some embodiments, provided herein are inhibitor-resistant luciferases comprising enhanced resistance to inhibition by dehydroluciferin compared to a luciferase of SEQ ID NO: 3. In some embodiments, the inhibitor-resistant luciferase exhibits a smaller relative reduction in activity when exposed to dehydroluciferin than a luciferase of SEQ ID NO: 3. In some embodiments, the inhibitor-resistant luciferase comprises at least 70% (e.g., 70%, 75%, 80%, 85%, 90%, 95%, 100%) sequence identity with SEQ ID NO: 3 and comprises at least one substitution relative to SEQ ID NO: 3 at a position selected from 240, 244, 254, 300, 344, and/or 396 of SEQ ID NO: 3. In some embodiments, the inhibitor-resistant luciferase comprises at least one substitution relative to SEQ ID NO: 3, the at least one substitution selected from I240L, H244R, Y254S, C300G, T344A, I396K, and/or conservative or semi-conservative variations of such substitutions. In some embodiments, the inhibitor-resistant luciferase comprises a substitution relative to SEQ ID NO: 3 at position 396 of SEQ ID NO: 3. In some embodiments, the inhibitor-resistant luciferase comprises an I396K substitution, or a conservative or semi-conservative variation thereof, relative to SEQ ID NO: 3.

In some embodiments, provided herein are inhibitor-resistant luciferases comprising enhanced resistance inhibition by to dehydroluciferin compared to a luciferase of SEQ ID NO: 1. In some embodiments, the inhibitor-resistant luciferase exhibits a smaller relative reduction in activity when exposed to dehydroluciferin than a luciferase of SEQ ID NO: 1. In some embodiments, the inhibitor-resistant luciferase comprises at least 70% (e.g., 70%, 75%, 80%, 85%, 90%, 95%, 100%) sequence identity with SEQ ID NO: 1 and comprises at least one substitution relative to SEQ ID NO: 1 at a position selected from 240, 244, 254, 300, 344, and/or 396 of SEQ ID NO: 1. In some embodiments, the inhibitor-resistant luciferase comprises at least one substitution relative to SEQ ID NO: 1, the at least one substitution selected from I240L, H244R, Y254S, C300G, T344A, I396K, and/or conservative or semi-conservative variations of such substitutions. In some embodiments, the inhibitor-resistant luciferase comprises a substitution relative to SEQ ID NO: 1 at position 396 of SEQ ID NO: 1. In some embodiments, the inhibitor-resistant luciferase comprises an I396K substitution, or a conservative or semi-conservative variation thereof, relative to SEQ ID NO: 1.

In some embodiments, the inhibitor-resistant luciferase comprises at least 70% (e.g., 70%, 75%, 80%, 85%, 90%, 95%, 100%) sequence identity with SEQ ID NO: 5 and comprises at least one substitution relative to SEQ ID NO: 3, said substitution at a position selected from 244, 300, and/or 396 of SEQ ID NO: 3. In some embodiments, the inhibitor-resistant luciferase comprises at least one substitution relative to SEQ ID NO: 3, the at least one substitution selected from H244R, C300G, I396K, and/or conservative or semi-conservative variations of such substitutions.

In some embodiments, the inhibitor-resistant luciferase comprises at least 70% (e.g., 70%, 75%, 80%, 85%, 90%, 95%, 100%) sequence identity with SEQ ID NO: 7 and comprises at least one substitution relative to SEQ ID NO: 3, said substitution at a position selected from 240, 254, 344, and/or 396 of SEQ ID NO: 3. In some embodiments, the inhibitor-resistant luciferase comprises at least one substitution relative to SEQ ID NO: 3, the at least one substitution selected from I240L, Y254S, T344A, I396K, and/or conservative or semi-conservative variations of such substitutions.

In some embodiments, the inhibitor-resistant luciferase comprises at least 70% (e.g., 70%, 75%, 80%, 85%, 90%, 95%, 100%) sequence identity with SEQ ID NO: 9 and comprises at least one substitution relative to SEQ ID NO: 3, said substitution at a position selected from 244, 344 and/or 396 of SEQ ID NO: 3. In some embodiments, the inhibitor-resistant luciferase comprises at least one substitution relative to SEQ ID NO: 3, the at least one substitution selected from H244R, T344A, I396K, and/or conservative or semi-conservative variations of such substitutions.

In some embodiments, the inhibitor-resistant luciferase comprises at least 70% (e.g., 70%, 75%, 80%, 85%, 90%, 95%, 100%) sequence identity with SEQ ID NO: 11 and comprises at least one substitution relative to SEQ ID NO: 3, said substitution at a position selected from 244, 300, 344 and/or 396 of SEQ ID NO: 3. In some embodiments, the inhibitor-resistant luciferase comprises at least one substitution relative to SEQ ID NO: 3, the at least one substitution selected from H244R, C300G, T344A, I396K, and/or conservative or semi-conservative variations of such substitutions.

In some embodiments, inhibitor-resistant luciferases comprise at least 10% (e.g., 10%, 15%, 20%, 25%, 30%, 35%, 40%, 45%, 50%, 55%, 60%, 65%, 70%, 75%, 80%, 85%, 90%, 95%, 100%, or more, or ranges therebetween) of the bioluminescent activity of a luciferase of SEQ ID NO: 3, when neither inhibitor-resistant luciferase nor the luciferase of SEQ ID NO: 3 have been exposed to dehydroluciferin.

In some embodiments, provided herein are reagent compositions comprising (i) an inhibitor-resistant luciferase described herein and (ii) luciferin. In some embodiments, a reagent composition further comprises a contaminant comprising a degradation product of luciferin. In some embodiments, the contaminant is dehydroluciferin. In some embodiments, a reagent composition further comprises magnesium. In some embodiments, a reagent composition further comprises one or more additional components selected from the group consisting of: a buffer, a defoamer, an ATPase inhibitor, an enzyme stabilizer, a detergent, an inhibitor of ATP-generating enzymes, a cell lysing agent, an ATP-extraction agent, co-enzyme A, a thiol reagent, a metal ion chelator, a protease inhibitor, and a salt. In some embodiments, the reagent composition is a single liquid reagent. In some embodiments, the reagent comprises racemic luciferin. In some embodiments, the reagent comprises dehydroluciferin. In some embodiments, racemic luciferin and/or dehydroluciferin are exogenously added to a reagent composition, for example, to improve the apparent stability of the luciferase, the overall stability of the reagent, and/or the duration of the luminescence signal produced by the reagent in the presence of ATP.

In some embodiments, provided herein are reagent compositions comprising an inhibitor-resistant luciferase described herein and a cationic detergent. In some embodiments, the cationic detergent is DTAB (dodecyltrimethylammonium bromide), CTAB (cetyltmethylammonium) Benzalkonium Chloride, or BDDABr (benzyldimethyldodecylammonium bromide).

In some embodiments, provided herein are kits comprising the reagent compositions described herein. In some embodiments, a kit further comprises one or more additional components selected from the group consisting of: a buffer, a defoamer, an ATPase inhibitor, an enzyme stabilizer, a detergent, an inhibitor of ATP-generating enzymes, a cell lysing agent, an ATP-extraction agent, co-enzyme A, a thiol reagent, a metal ion chelator, a protease inhibitor, and a salt. In some embodiments, a kit further comprises instructions for performing an ATP detection or quantification assay.

In some embodiments, provided herein are assay systems for detecting or quantifying ATP in a sample, comprising: (a) a reagent composition described herein; and (b) a sample comprising or suspected of comprising ATP. In some embodiments, assay systems further comprise a device for the detection and/or measurement of luminescence (e.g., luminometer although other light detection device or instrument may be used). In some embodiments, the sample is a cell lysate.

In some embodiments, provided herein are methods of detecting ATP in a sample comprising: (a) adding to the sample a reagent composition reagent composition described herein; and (b) detecting luminescence. In some embodiments, the sample comprises cells, and the method further comprises lysing the cells to generate a cell lysate.

In some embodiments, provided herein are methods of quantifying the amount or concentration of ATP in a sample comprising: (a) adding to the sample a reagent composition reagent composition described herein; (b) quantifying luminescence from the sample; and (c) comparing the luminescence to a control value to determine the amount or concentration of ATP in the sample. In some embodiments, the control value is determined from a separate quantification of luminescence produced by a control sample comprising a known concentration of ATP. In some embodiments, methods further comprise the step of adding a known concentration of ATP to the sample. In some embodiments, luminescence is quantified at multiple time-points. In some embodiments, luminescence is quantified in real time.

In some embodiments, provided herein is the use of a reagent composition described herein for the detection and/or quantification of ATP in a sample.

In some embodiments, provided herein are methods of enhancing the apparent signal stability of an inhibitor-resistant luciferase described herein in an assay, comprising performing the assay with one or more inhibitors of the luciferase present. In some embodiments, the inhibitor is selected from one or more of a dehydroluciferin, an oxoluciferin, and L-luciferin. In some embodiments, the inhibitor-resistant luciferase exhibits an increase in enhancement of apparent signal stability compared to a native, wild-type version the luciferase.

DEFINITIONS

Figure 1:
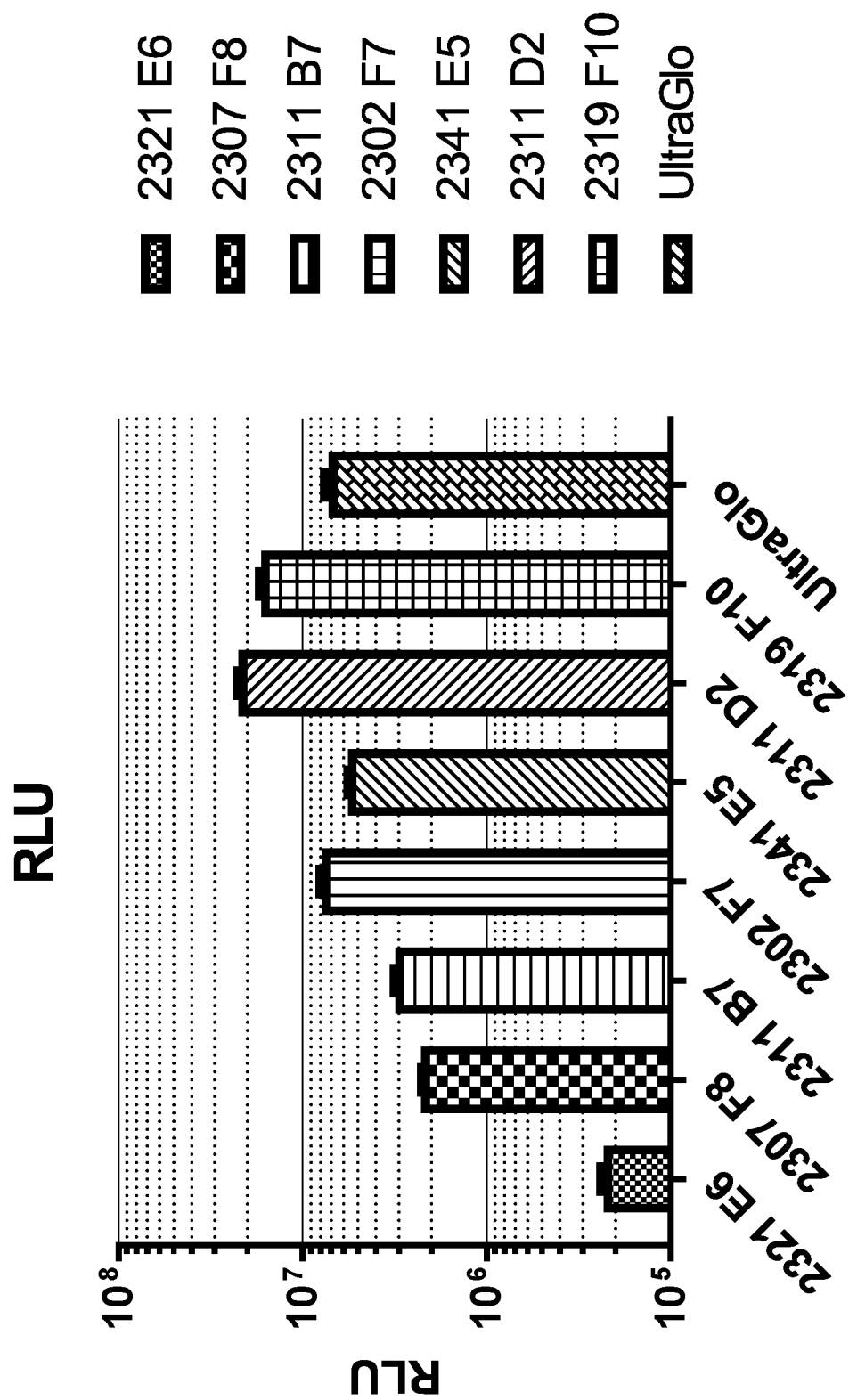
FIG. 1 shows a graph depicting the luminescence as measure by relative light unit (RLU) of variant luciferases and ULTRAGLO luciferase (Promega Corp., Madison, Wis.).

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a luciferase" is a reference to one or more luciferases and equivalents thereof known to those skilled in the art, and so forth.

As used herein, the term "enhanced" refers to an improvement in a particular property relative to that of a reference. For example, when used to describe a property of a luciferase variant (e.g., luminescence, signal stability, biocompatibility, protein stability (e.g., enzyme stability), or protein expression), "enhanced" refers to an improvement (e.g., 1%, 2%, 5%, 10%, 20%, 25%, 50%, 75%, 2-fold, 3-fold, 4 fold, 5-fold, 10 fold, 20-fold, 50-fold, 100-fold, 200-fold, 500-fold, 1000-fold, or more, or ranges therebetween) in that property compared to a reference luciferase, such as a native/wild-type version of that luciferase (e.g., SEQ ID NO: 1). A variant luciferase may exhibit one or more of "enhanced luminescence," "enhanced signal stability," "enhanced enzyme stability," "enhanced protein expression," etc.

As used herein, the term "signal duration" refers to the persistence of a signal, for example, as measured by the half-life of decay of the signal in a time-course or the length of time a signal remains constant (e.g., before detectable decay). The term "signal stability" refers to the characteristic signal duration of an enzyme (e.g., a luciferase).

"Enhanced signal stability" refers to an increase in signal duration (e.g. the persistence of a signal intensity (e.g., luminescent signal) from an enzyme (e.g., a luciferase combined with luciferin and ATP) compared to a reference enzyme (e.g., compared to a wild-type version of the luciferase (e.g., SEQ ID NO: 1) combined with luciferin and ATP)).

As used herein, the term "apparent signal stability" refers to the persistence of a signal (e.g., luminescence) from an enzyme (e.g., luciferase combined with luciferin and ATP) under a particular set of conditions (e.g., in the presence of an inhibitor). "Enhanced apparent signal stability" refers to an increase in the persistence of a signal (e.g., luminescent signal) from an enzyme (e.g., a luciferase) combined with luciferin and ATP under a particular set of conditions compared to the persistence of that same enzyme combined with luciferin and ATP under reference conditions. For example, a variant luciferase combined with luciferin and ATP may exhibit enhanced apparent signal stability in the presence of an inhibitor (e.g., by lowering the initial signal from the luciferase, the loss of signal over a time course is reduced). In some embodiments, a variant enzyme combined with luciferin and ATP exhibits "an increase in enhancement of apparent signal stability" when the variant luciferase combined with luciferin and ATP exhibits a greater enhancement of apparent signal stability compared to a reference luciferase (e.g., compared a wild-type version of the luciferase (e.g., SEQ ID NO: 1)) combined with luciferin and ATP.

As used herein, the term "storage stability" refers to the consistency of the signal (e.g., luminescence) from an enzyme (e.g., luciferase with luciferin and ATP) when measured at various points in time (e.g., end-point measurements). For example, luminescence of aliquots of a stored luciferase (e.g., stored in an aqueous solution along with substrate) are measured (e.g., in the presence of luciferin and ATP) at various time-points relevant to the storage of the luciferase (e.g., days, weeks, etc.), and an enzyme or set of conditions that result in more consistency (e.g., less loss of signal, longer duration before decay, etc.) over time exhibits "enhanced storage stability." A variant enzyme (e.g., an inhibitor resistant variant) may exhibit enhanced storage stability relative to a wild-type enzyme, and/or a particular set of conditions (e.g., in the presence of inhibitor) may result in enhanced storage stability relative to reference conditions. Some luciferases exhibit limited storage stability when stored in the presence of luciferin, due to the formation of luciferin breakdown products that are inhibitory to the luciferase. In some embodiments, inhibitor-resistant luciferases exhibit increased storage stability. In some embodiments, storage conditions comprising both luciferin substrate and inhibitor (e.g., dehydroluciferin, fluorodehydroluciferin, aminodehydroluciferin, L-luciferin, etc.) result in enhanced storage stability, for example, by decreasing early time-point signal to more closely reflect late time-point signals.

As used herein, the terms "inhibitor resistant" and "enhanced resistance to inhibitor" refers to an enzyme that retains more activity in the presence of an inhibitor or enzyme activity than a reference version of the enzyme (e.g., a native wild-type version of the enzyme). An inhibitor-resistant enzyme is not necessarily 100% resistant to inhibitor. For example, an "inhibitor-resistant luciferase" is a polypeptide that retains more (e.g., e.g., exhibits a smaller percentage loss) luciferase activity (e.g., conversion of luciferin to oxyluciferin, RLU output, etc.) in the presence of ATP and a luciferase inhibitor (e.g., dehydroluciferin, fluorodehydroluciferin, aminodehydroluciferin, L-luciferin, etc.) when compared to a wild-type version of the luciferase (e.g., SEQ ID NO: 1).

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("Octan"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "polypeptide" refers to a polymer of amino acids linked together by peptide bonds that is greater than about 50 amino acids in length. Polypeptides may comprise natural amino acids, non-natural amino acids, amino acid analogs and/or modified amino acids, and may be a naturally occurring sequence, or a non-natural (artificial) sequence, or a subsequence of naturally occurring protein or a non-natural (artificial) sequence.

As used herein, the term "artificial" refers to compositions and systems that are designed or prepared by man, and are not naturally occurring. For example, an artificial sequence refers to a amino acid or nucleotide sequence that does not occur in nature (e.g., a polypeptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least Y % sequence identity with SEQ ID NO:Z" may have up to X substitutions relative to SEQ ID NO:Z, and may therefore also be expressed as "having X or fewer substitutions relative to SEQ ID NO:Z."

As used herein, the term "enzyme stability" refers to the capacity of an enzyme to remain active following exposure to a particular set of conditions (e.g., temperature, pH, ionic concentration, inhibitory agents, etc.). For example, an enzyme that exhibits enhanced stability relative to a control enzyme exhibits a smaller loss of activity upon exposure to a set of conditions than the control enzyme.

As used herein, the term "luciferin" refers to a compound, having the structure:

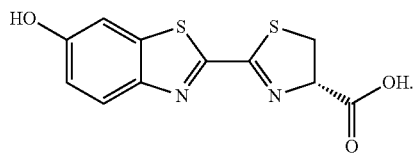 [SMILES: O=C(O)[C@H]1CSC(c2nc3ccc(O)cc3s2)=N1]

Luciferin may be present as "L-luciferin" or "D-luciferin" or a racemic mixture of L- and D-form luciferin. Unless specified otherwise (e.g., "L-luciferin," "a racemic luciferin mixture," etc.), the term "luciferin: refers to the D-form. The term "luciferins" refers more broadly to a class of bioluminescent compounds (or chiral sisters thereof) that serve as substrates for firefly luciferases, and include natural artificial derivatives of luciferin, such as aminoluciferin, fluoroluciferin, etc.

As used herein, the term "luciferin derivative" refers to a class of compounds that are structurally related to luciferin, having similar ring structure, and similar, but not necessarily identical, substitutes. Luciferin derivatives typically differ from luciferin by the presence or absence of double bonds in the ring structure, and or the presence or different substituents (e.g., halogen group, oxo group, amino group, OH group, $CH_3$ group, CN, etc.). Some luciferin derivatives are substrates of firefly luciferase, others are inhibitors of firefly luciferase.

As used herein, the term "luciferin reaction product" refers to luciferin derivatives that are not substrates for a firefly luciferase, the production of which from a luciferin is catalyzed by a luciferase (e.g., a firefly luciferase) in a light-producing reaction. Examples of luciferin reaction products include oxyluciferin, aminooxyluciferin, fluorooxyluciferin, etc.

As used herein, the term "luciferin degradation product" refers to luciferin derivatives that are not substrates for a firefly luciferase, the production of which occurs by chemical degradation of a luciferin, in a reaction that is typically not catalyzed by a luciferase and does not result in significant light production. Examples of luciferin reaction products include deydroluciferin, aminodehydroluciferin, fluorodehydroluciferin, etc.

The term "sample" is used herein in its broadest sense. It is meant to include: a specimen, culture, lysate, etc. It includes a prepared solution or mixture, and both biological and environmental samples. Biological samples may take the form of a fluid or solid, and may be obtained from any suitable biological source (e.g., animal, including human, microbiological, etc.). Environmental samples include environmental material such as surface matter, soil, plants, and water. These examples are not to be construed as limiting the sample types applicable to the present invention.

DETAILED DESCRIPTION

Provided herein are inhibitor-resistant luciferases and methods of use thereof. In particular, luciferases are provided that are thermal stable and exhibit improved resistance to inhibition by luciferin break-down products such as dehydroluciferin.

In some embodiments, provided herein are luciferases that are thermally stable (e.g., stable at storage temperatures above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween)). In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when stored at temperatures above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween). In some embodiments, a luciferase herein exhibits enhanced thermal stability relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following storage at temperatures above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween).

In some embodiments, provided herein are luciferases that are thermally stable (e.g., stable at incubation temperatures above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween)). In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity following incubation temperatures above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween) for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween). In some embodiments, a luciferase herein exhibits enhanced thermal stability relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following incubation temperatures above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween) for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween).

In some embodiments, luciferases herein are stable when stored in the presence of luciferin (e.g., D-luciferin, racemic luciferin mix) and/or luciferin derivatives (e.g., fluoroluciferin, aminoluciferin, etc.). In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when stored in the presence of luciferin and/or luciferin derivatives (e.g., fluoroluciferin, aminoluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween). In some embodiments, a luciferase herein exhibits enhanced stability in the presence of luciferin and/or luciferin derivatives (e.g., fluoroluciferin, aminoluciferin, etc.) relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following storage in the presence of luciferin and/or luciferin derivatives (e.g., fluoroluciferin, aminoluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween).

In some embodiments, luciferases herein are stable in the presence of luciferin break-down products (e.g., dehydroluciferin) and/or the breakdown products of luciferin derivatives (e.g., fluorodehydroluciferin, aminodehydroluciferin, etc.). In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when stored in the presence of luciferin break-down products (e.g., dehydroluciferin) and/or the breakdown products of luciferin derivatives (e.g., fluorodehydroluciferin, aminodehydroluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween). In some embodiments, a luciferase herein exhibits enhanced resistance to inhibition by luciferin break-down products (e.g., dehydroluciferin) and/or the breakdown products of luciferin derivatives (e.g., fluorodehydroluciferin, aminodehydroluciferin, etc.) relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following storage in the presence of luciferin break-down products (e.g., dehydroluciferin) and/or the breakdown products of luciferin derivatives (e.g., fluorodehydroluciferin, aminodehydroluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween).

In some embodiments, luciferases herein are stable in the presence of L-luciferin and/or a racemic luciferin mix. In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when stored in the presence of L-luciferin and/or a racemic luciferin mix for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween). In some embodiments, a luciferase herein exhibits enhanced resistance to inhibition by L-luciferin and/or a racemic luciferin mix relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following storage in the presence of L-luciferin and/or a racemic luciferin mix for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween).

In some embodiments, luciferases herein are thermally stable when stored in the presence of luciferin (e.g., D-luciferin, racemic luciferin mix) and/or luciferin derivatives (e.g., fluoroluciferin, aminoluciferin, racemic luciferin, etc.). In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when stored above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween) in the presence of luciferin (e.g., D-luciferin, racemic luciferin mix) and/or luciferin derivatives (e.g., fluoroluciferin, aminoluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween). In some embodiments, a luciferase herein exhibits enhanced thermal stability in the presence of luciferin (e.g., D-luciferin, racemic luciferin mix) and/or luciferin derivatives (e.g., fluoroluciferin, aminoluciferin, etc.) relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following storage above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween) in the presence of luciferin (e.g., D-luciferin, racemic luciferin mix) and/or luciferin derivatives (e.g., fluoroluciferin, aminoluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween).

In some embodiments, luciferases herein are thermally stable in the presence of luciferin break-down products (e.g., dehydroluciferin) and/or break-down products of luciferin derivatives (e.g., aminodehydroluciferin, fluorodehydroluciferin, etc.). In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when stored above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween) in the presence of luciferin break-down products (e.g., dehydroluciferin) and/or break-down products of luciferin derivatives (e.g., aminodehydroluciferin, fluorodehydroluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween). In some embodiments, a luciferase herein exhibits enhanced thermal stability in the presence of luciferin break-down products (e.g., dehydroluciferin) and/or break-down products of luciferin derivatives (e.g., aminodehydroluciferin, fluorodehydroluciferin, etc.) relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following storage above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26°

C., 27° C., 28° C., 29° C., 30° C., 31° C., 32° C., 33° C., 34° C., 35° C., 36° C., 37° C., 38° C., 39° C., 40° C., or ranges therebetween) in the presence of luciferin break-down products (e.g., dehydroluciferin) and/or break-down products of luciferin derivatives (e.g., aminodehydroluciferin, fluorodehydroluciferin, etc.) for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween).

In some embodiments, luciferases herein are thermally stable in the presence of L-luciferin and/or a racemic luciferin mix. In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when stored above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween) in the presence of L-luciferin and/or a racemic luciferin mix for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween). In some embodiments, a luciferase herein exhibits enhanced thermal stability in the presence of L-luciferin and/or a racemic luciferin mix relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following storage above 0° C. (e.g., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or ranges therebetween) in the presence of L-luciferin and/or a racemic luciferin mix for 1 to 365 days (e.g., 1 day, 2 days, 5 days, 10 days, 20 days, 30 days, 40 days, 50 days, 75 days, 100 days, 150 days, 200 days, 250 days, 300 days, 350 days, 365 days, or ranges therebetween).

In some embodiments, luciferases herein are thermally stable when incubated in the presence of luciferin. In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when incubated above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween) in the presence of luciferin for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween). In some embodiments, a luciferase herein exhibits enhanced thermal stability when incubated in the presence of luciferin relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following incubation above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., C., 48° C., 49° C., 50° C. or ranges therebetween) in the presence of luciferin for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween).

In some embodiments, luciferases herein are thermally stable when incubated in the presence of luciferin break-down products (e.g., dehydroluciferin) and/or break-down products of luciferin derivatives (e.g., aminodehydroluciferin, fluorodehydroluciferin, etc.). In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when incubated above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween) in the presence of luciferin break-down products (e.g., dehydroluciferin) and/or break-down products of luciferin derivatives (e.g., aminodehydroluciferin, fluorodehydroluciferin, etc.) for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween). In some embodiments, a luciferase herein exhibits enhanced thermal stability when incubated in the presence of luciferin break-down products (e.g., dehydroluciferin) and/or break-down products of luciferin derivatives (e.g., aminodehydroluciferin, fluorodehydroluciferin, etc.) relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following incubation above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween) in the presence of luciferin break-down products (e.g., dehydroluciferin) and/or break-down products of luciferin derivatives (e.g., aminodehydroluciferin, fluorodehydroluciferin, etc.) for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween).

In some embodiments, luciferases herein are thermally stable when incubated in the presence of L-luciferin and/or a racemic luciferin mix. In some embodiments, a luciferase herein exhibits less than 20% (e.g., 19%, 18%, 17%, 16%, 15%, 14%, 13%, 12%, 11%, 10%, 9%, 8%, 7%, 6%, 5%, 4%, 3%, 2%, 1%, or less, or ranges therebetween (e.g., 5% or less)) loss of activity when incubated above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween) in the presence of L-luciferin and/or a racemic luciferin mix for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween). In some embodiments, a luciferase herein exhibits enhanced thermal stability when incubated in the presence of L-luciferin and/or a racemic luciferin mix relative to a luciferase of SEQ ID NO: 1 and/or SEQ ID NO: 3. In some embodiments, a luciferase of SEQ ID NO: 1 and/or SEQ ID NO: 3 exhibits reduced activity relative to a luciferase herein following incubation above room temperature (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or ranges therebetween) in the presence of L-luciferin and/or a racemic luciferin mix for 1 to 100 minutes (e.g., 1 minute, 2 minutes, 5 minutes, 10 minutes 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, or ranges therebetween).

In some embodiments, luciferases described herein are resistant to inhibition by one or more (e.g., 2, 3, 4, 5, 6, 7, 8, 9, 10, or more, or ranges therebetween) luciferin breakdown products, luciferin reaction products, and other non-substrate (e.g., not a luciferase (e.g., firefly luciferase) substrate) luciferin derivatives, such as, dehydroluciferin, aminodehydroluciferin, fluorodehydroluciferin, L-luciferin, oxoluciferin, fluorooxoluciferin, aminooxoluciferin, etc. Experiments conducted during development of embodiments herein to engineer (e.g., evolve) dehydroluciferin that have improved resistance to inhibition by luciferin breakdown products (e.g., compounds that result from storage and/or incubation of luciferin).

In some embodiments, a thermally-stable and/or inhibitor-resistant (e.g., dehydroluciferin-resistant) luciferase comprises 1 or more (e.g., 1, 2, 3, 4, 5, 6, 7, 8, 9, 10, 15, 20, 25, 30, 35, 40, 45, 50, 60, 70, 80, 90, 100, or more, or ranges therebetween) substitutions relative to a wild-type firefly luciferase (SEQ ID NO: 1).

In some embodiments, a thermally-stable and/or inhibitor-resistant (e.g., dehydroluciferin-resistant) luciferase comprises 1 or more (e.g., 1, 2, 3, 4, 5, 6, 7, 8, 9, 10, 15, 20, 25, 30, 35, 40, 45, 50, 60, 70, 80, 90, 100, or more, or ranges therebetween) substitutions relative to a luciferase of SEQ ID NO: 3.

In some embodiments, a luciferase described herein exhibits enhanced signal stability (e.g., as measured by the half-life of decay of the signal in a time-course (e.g., 10% increase, 20% increase, 30% increase, 40% increase, 50% increase, 60% increase, 70% increase, 80% increase, 90% increase, 2-fold increase, 3-fold increase, 4-fold increase, 5-fold increase, 6-fold increase, 7-fold increase, 8-fold increase, 9-fold increase, 10-fold increase, 20-fold increase, 50-fold increase, 100-fold increase, 1000-fold increase, or more, or ranges therebetween)) when compared to a reference luciferase (e.g., a native, wild-type luciferase (e.g., SEQ ID NO: 1), an enhanced synthetic luciferase (e.g., SEQ ID NO: 3), etc.).

In some embodiments, a luciferase described herein exhibits enhanced apparent signal stability (e.g., as measured by the half-life of decay of the signal in a time-course (e.g., 10% increase, 20% increase, 30% increase, 40% increase, 50% increase, 60% increase, 70% increase, 80% increase, 90% increase, 2-fold increase, 3-fold increase, 4-fold increase, 5-fold increase, 6-fold increase, 7-fold increase, 8-fold increase, 9-fold increase, 10-fold increase, 20-fold increase, 50-fold increase, 100-fold increase, 1000-fold increase, or more, or ranges therebetween)) in the presence of an inhibitor when compared to its stability in the absence of the inhibitor. In some embodiments, the inhibitor is one or more of a dehydroluciferin (e.g., dehydroluciferin, dehydrooxoluciferin, dehydroaminoluciferin, dehydroaminooxoluciferin, and L-luciferin In some embodiments, a luciferase described herein exhibits an increase in enhancement of apparent signal stability (e.g., as measured by the half-life of decay of the signal in a time-course (e.g., 10% increase, 20% increase, 30% increase, 40% increase, 50% increase, 60% increase, 70% increase, 80% increase, 90% increase, 2-fold increase, 3-fold increase, 4-fold increase, 5-fold increase, 6-fold increase, 7-fold increase, 8-fold increase, 9-fold increase, 10-fold increase, 20-fold increase, 50-fold increase, 100-fold increase, 1000-fold increase, or more, or ranges therebetween)) in the presence of an inhibitor when compared to its stability in the absence of the inhibitor, when compared to the signal stability enhancement in the presence of the inhibitor of a reference luciferase (e.g., a native, wild-type luciferase (e.g., SEQ ID NO: 1), an enhanced synthetic luciferase (e.g., SEQ ID NO: 3), etc.).

In some embodiments, a luciferase comprises a substitution at amino acid position 244, relative to SEQ ID NO: 3. In some embodiments, a luciferase comprises a H244R substitution relative to SEQ ID NO: 3. In some embodiments, a luciferase comprises a substitution at amino acid position 300, relative to SEQ ID NO: 3. In some embodiments, a luciferase comprises a C300G substitution relative to SEQ ID NO: 3. In some embodiments, a luciferase comprises a substitution at amino acid position 396, relative to SEQ ID NO: 3. In some embodiments, a luciferase comprises a I396K substitution relative to SEQ ID NO: 3. In some embodiments, a luciferase comprises a substitution at nucleotide position 222, relative to SEQ ID NO: 4. In some embodiments, a luciferase comprises a C to T substitution at nucleotide position 222 relative to SEQ ID NO: 4.

In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence identity with SEQ ID NO: 5. In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence similarity (e.g., conservative or semi-conservative) with SEQ ID NO: 5. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) substitutions relative to SEQ ID NO: 5. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) non-conservative substitutions relative to SEQ ID NO: 5. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) semi-conservative substitutions relative to SEQ ID NO: 5. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) conservative substitutions relative to SEQ ID NO: 5.

In some embodiments, a luciferase comprises a substitution at amino acid position 240, relative to SEQ ID NO: 3. In some embodiments, a luciferase comprises a I240L substitution relative to SEQ ID NO: 3. In some embodiments, a luciferase comprises a substitution at amino acid position 254, relative to SEQ ID NO: 3. In some embodiments, a luciferase comprises a Y254S substitution relative to SEQ ID NO: 3. In some embodiments, a luciferase comprises a substitution at amino acid position 344, relative to SEQ ID NO: 3. In some embodiments, a luciferase comprises a T344A substitution relative to SEQ ID NO: 3. In some embodiments, a luciferase comprises a substitution at amino acid position 396, relative to SEQ ID NO: 3. In some embodiments, a luciferase comprises a I396K substitution relative to SEQ ID NO: 3.

In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence identity with SEQ ID NO: 7. In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence similarity (e.g., conservative or semi-conservative) with SEQ ID NO: 7. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) substitutions relative to SEQ ID NO: 7. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) non-conservative substitutions relative to SEQ ID NO: 7. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) semi-conservative substitutions relative to SEQ ID NO: 7. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) conservative substitutions relative to SEQ ID NO: 7.

In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence identity with SEQ ID NO: 9. In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence similarity (e.g., conservative or semi-conservative) with SEQ ID NO: 9. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) substitutions relative to SEQ ID NO: 9. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) non-conservative substitutions relative to SEQ ID NO: 9. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) semi-conservative substitutions relative to SEQ ID NO: 9. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) conservative substitutions relative to SEQ ID NO: 9.

In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence identity with SEQ ID NO: 11. In some embodiments, a thermally-stable and/or inhibitor-resistant (e.g., dehydroluciferin-resistant) luciferase comprises at least 70% (e.g., 70%, 75%, 80%, 85%, 90%, 95%, 96%, 97%, 98%, 99%, 100%, or ranges therebetween) sequence similarity (e.g., conservative or semi-conservative) with SEQ ID NO: 11. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) substitutions relative to SEQ ID NO: 11. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) non-conservative substitutions relative to SEQ ID NO: 11. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) semi-conservative substitutions relative to SEQ ID NO: 11. In some embodiments, a luciferase comprises 100 or fewer (e.g., 0, 1, 2, 3, 4, 5, 6, 7, 8, 9, 10, 15, 20, 25, 30, 35, 40, 45, 50, 60, 70, 80, 90, 100, or ranges therebetween) conservative substitutions relative to SEQ ID NO: 11.

In some embodiments, a luciferase herein comprises any combination of amino acid substitutions relative to SEQ ID NO: 3, such as those selected from positions 240, 244, 254, 300, 344, and 396. In some embodiments, a luciferase herein comprises any combination of amino acid substitutions relative to SEQ ID NO: 3, such as I240L, H244R, Y254S, C300G, T344A, I396K, and/or conservative or semi-conservative variations of such substitutions.

In some embodiments, provided herein is a luciferase comprising at least 70% sequence identity to SEQ ID NO: 3, but having at least one substitution at a position corresponding to 240, 244, 254, 300, 344, and/or 396 of SEQ ID NO: 3. In some embodiments, provided herein is a luciferase comprising at least 70% sequence identity to SEQ ID NO: 3, but having at least one substitution corresponding to I240L, H244R, Y254S, C300G, T344A, I396K, and/or conservative or semi-conservative variations of such substitutions. In some embodiments, a luciferase comprises a substitution at position 396 (e.g., an I396K substitution).

In some embodiments, provided herein are nucleic acids (e.g., DNA, RNA, etc.) encoding the polypeptides described herein. In some embodiments, provided herein are vectors comprising nucleic acids (e.g., DNA, RNA, etc.) encoding the polypeptides described herein. In some embodiments, provided herein are cells expression the polypeptides described herein. In some embodiments, provided herein are fusion proteins comprising the polypeptides described herein.

In some embodiments, to measure luminescence and thereby determine the activity of a particular luciferase (or reagent composition comprising a luciferase), the relative light unit (RLU) value generated by the luciferase reaction at a timepoint of interest after the reagent composition is combined with a sample may be measured. In some embodiments, the relative light output may be compared to a control value (e.g., to determine the stability of the activity of the luciferase).

In some embodiments, the luciferases described herein exhibit enhanced stability and/or activity in the presence of break-down products of luciferin (e.g., compounds that inhibit ATP-dependent luciferases that utilize luciferin as a substrate (e.g., dehydroluciferin, etc.), etc.). In some embodiments, this enhanced stability allows the luciferases herein to be in contact with (e.g., stored with) luciferin under conditions (e.g., >0° C., 10° C., 15° C., 20° C., 25° C., 30° C., 35° C., 40° C., 45° C., 50° C., or more) that result in the production of luciferin degradation products over time (e.g., 1 day, 2 days, 3 days, 4 days, 5 days, 6 days, 7 days, 8 days, 9 days, 10 days, 12 days, 14 days, 16 days, 18, days, 20 days, 25 days, 30 days, 40 days, 50 days, 75 days, 100 days, 150 days, 200 days, 250 days, 300 days, 365 days, or more). As such, in some embodiments, provided herein are stable reagent compositions comprising a luciferase described herein and luciferin. In some embodiments, reagent compositions are provided comprising a luciferase described herein, luciferin, and one or more luciferin degradation products (e.g., dehydroluciferin, etc.).

In some embodiments, reagent compositions described herein (e.g., comprising a luciferase and luciferin) are useful in a variety of assays, including for the detection of ATP in a sample. Because the bioluminescence of the luciferases described herein is dependent upon the presence of luciferin and ATP, contacting a sample comprising ATP with a reagent composition herein (e.g., comprising luciferase and luciferin) results in detectable bioluminescence. In some embodiments, because the luciferases described herein are resistant to inhibition by luciferin degradation products, such reagent compositions maintain activity over time and are useful in the quantification of ATP in sample over time (e.g., the activity of the reagent composition does not decrease (e.g., loss of activity is reduced compared to other luciferases)).

In some embodiments, in addition to a luciferase described herein and luciferin (and potentially luciferin degradation products), reagent compositions further comprise additional components for storage (e.g., for enzyme stability), handling (e.g., to facilitate dispensing of the reagent composition), and/or assay performance. In some embodiments, a reagent composition additional comprises salts or metal ions (e.g., $Mg^{2+}$), detergents, buffers, etc. In some embodiments, additional components are part of the reagent composition, and stored in the same container at the luciferase and luciferin. In some embodiments, a reagent composition (e.g., comprising luciferase and luciferin) is provided as part of a kit, the kit comprising additional components/reagents that are stored in a separate contained from the reagent composition.

In some embodiments, a kit or reagent composition comprises a luciferase described herein and aminothiothymidine (ATT). In some embodiments, a kit or reagent composition comprises a luciferase described herein and dehydroluciferin. In some embodiments, a kit or reagent composition comprises a luciferase described herein, ATT, and dehydroluciferin. In some embodiments, a kit or reagent composition comprises a luciferase described herein, D-luciferin, and ATT. In some embodiments, a kit or reagent composition comprises a luciferase described herein, D-luciferin, and dehydroluciferin. In some embodiments, a kit or reagent composition comprises a luciferase described herein, D-luciferin, ATT, and dehydroluciferin. In some embodiments, a kit or reagent composition comprises a luciferase described herein and a racemic luciferin mixture. In some embodiments, a kit or reagent composition comprises a luciferase described herein and a racemic luciferin mixture. In some embodiments, a kit or reagent composition comprises a luciferase described herein, dehydroluciferin, and a racemic luciferin mixture. In some embodiments, a kit or reagent composition comprises a luciferase described herein, ATT, and a racemic luciferin mixture. In some embodiments, a kit or reagent composition comprises a luciferase described herein, ATT, dehydroluciferin, and a racemic luciferin mixture. In any of the aforementioned embodiments, luciferin may be replaced by other luciferin substrates (e.g., aminoluciferin, fluoroluciferin, etc.) and/or dehydroluciferin may be replaced by other luciferin degradation products (e.g., aminodehydroluciferin, fluorodehydroluciferin, etc.

In some embodiments, a kit or reagent composition comprises a luciferase (e.g., inhibitor resistant luciferase), luciferin (e.g., D-luciferin), and one or more inhibitors of the luciferase (e.g., dehydroluciferin, aminodehydroluciferin, fluorodehydroluciferin, L-luciferin, etc.). In some embodiments, inclusion of one or more inhibitors of the luciferase in the kit or reagent composition provides enhancement of one or more of signal duration, apparent enzyme stability, and/or storage stability. In some embodiments, the enhanced resistance of the luciferase to inhibitor provides a reagent composition or kit with one or more of enhanced signal duration, enhanced apparent enzyme stability, and/or enhanced storage stability, while providing sufficient signal (e.g., due to the inhibitor resistance) to be useful in assays and other applications.

In some embodiments, a kit or reagent composition comprises between 10:1 and 1:10 ratio (e.g., 10:1, 9:1, 8:1, 7:1, 6:1, 5:1, 4:1, 3:1, 2:1, 1:1, 1:2, 1:3, 1:4, 1:5, 1:6, 1:7, 18, 1:9, 1:10, or ranges therebetween) of D-luciferin (and/or D-luciferin-related substrate (e.g., aminoluciferin, fluoroluciferin, etc.) to inhibitor (e.g., dehydroluciferin, aminodehydroluciferin, fluorodehydroluciferin, L-luciferin, etc.). In some embodiments, a luciferin:inhibitor ratio is selected to minimize the net gain of inhibitor (e.g., dehyro breakdown products) over a relevant timescale (e.g., over the course of an assay (e.g., 1 minute, 5 minutes, 10 minutes, 20 minutes, 40 minutes, 1 hour, 2 hours, 4 hours, 6 hours, 12 hours, or more, or ranges therebetween), over the course of storage (e.g., 1 day, 2 days, 4 days, 6 days, 8 days, 10 days, 15 days, 20 days, 30 days, 40 days, 60 days, 80 days, 100 days, 150 days, 200 days, 300 days, or more, ore ranges therebetween), etc.). In some embodiments, conditions affecting the optimal ratio of luciferin:inhibitor include the kinetics of the luciferase and the starting or storage concentration of the luciferin.

In some embodiments, a kit or reagent composition comprises one or more suitable buffers. Any buffers that maintain suitable pH for the working solution and do not significantly interfere with the luciferase-luciferin reaction are contemplated. The preferred pH range is between about pH 4.5 and about pH 9.0 (e.g., about pH 6.0 and about pH 8.0 (e.g., 6.0, 6.2, 6.4, 6.6, 6.8, 7.0, 7.2, 7.4, 7.6, 7.8, 8.0, and ranges therebetween)). Suitable buffers include MES, citrate buffers, phosphate buffered saline (PBS), Tris-N-(2-Hydroxyethyl)piperazine-N'-(2-ethanesulfonic acid) (HEPES), piperazine-1,4-bis(2-ethanesulfonic acid) (PIPES), borate, and any other buffer known to those of skill in the art may be suitable. Selection of appropriate buffers depends on pH buffering capacity and interaction with the luciferase-luciferin reaction.

In some embodiments, a kit or reagent composition comprises one or more defoamers. Defoaming agents are desirable to prevent foam from interfering with the detection of bioluminescence, especially in applications that quantify luminescence. Defoming agents, such as MAZU, may be organic or silicone based. Selection of defoamers depends on their ability to eliminate foam without interfering with the luciferase-luciferin reaction.

In some embodiments, a kit or reagent composition comprises magnesium. The luciferase-luciferin reaction is dependent not only on ATP, but also on magnesium ions. In some embodiments, to ensure luciferase activity, magnesium is exogenously supplied. In addition to magnesium sulfate, other salts of magnesium are contemplated, such as magnesium chloride, magnesium gluconate, magnesium acetate, magnesium bromide, magnesium carbonate, or any magnesium complex that dissociates in the reagent composition or in the sample to yield Mg' ions available to the luciferase and does not interfere with the luciferase-luciferin reaction. In some embodiments, other cations are provided in addition to or in place of magnesium, such as calcium and manganese. In some embodiments, the endogenous magnesium of the sample is sufficient to allow the luciferase-luciferin bioluminescence in the presence of ATP; in such embodiments, magnesium may not be included in a kit or reagent composition.

In some embodiments, a kit or reagent composition comprises a component containing one or more ATPase inhibitors within a solution optionally containing other functional components, such as buffers, defoamers, enzyme stabilizers, and the like. This component may be supplied as a working solution or as a concentrate. In some embodiments, an ATPase inhibitor is a detergent with a charged group (e.g., cationic detergent (e.g., DTAB (dodecyltrimethylammonium bromide), Benzalkonium Chloride, CTAB (cetyltmethylammonium), BDDABr (benzyldimethyldodecylammonium bromide), etc.), anionic detergent (e.g., deoxycholate or SDS) or zwitterionic detergent (e.g., sulfobetaine 3-10), etc.). Such inhibitors prevent ATPases in a sample from processing ATP to adenosine diphosphate (ADP) and adenosine monophosphate (AMP), for example, before the luciferase is able to utilize the ATP in the luciferase-luciferin reaction. ATPase inhibitors may inactivate ATPases directly or indirectly. They may bind to ATPases, either in the active sites, thus preventing substrate binding, or denature ATPases, such as by denaturing detergents, or they may selectively sequester ATPases from their substrates.

In some embodiments, a kit or reagent composition comprises a component containing one or more inhibitors of ATP-generating enzymes. In some samples, enzymes such as kinases may be active, allowing for continued production of ATP. Because the ATP concentration is determined at a specific time, such enzymatic activity may result in an overestimation of the ATP concentration. In some embodiments, to counter such ATP-generating activity, reagent compositions and/or kits herein comprise inhibitors of ATP production. Examples of useful compounds include NaF, which is useful at concentrations of at least 1 mM, 2 mM, 5 mM, 10 mM 20 mM 50 mM, 100 mM or more, or ranges therebetween. Any such inhibitor may be used, however, if it does not adversely affect luciferase so as to take it outside the utility of embodiments herein. Other inhibitors of ATP-generating enzymes include, but are not limited to, vanadate, paranitrophenylphosphate and dichloroacetic acid.

In some embodiments, a kit or reagent composition comprises a cell lysing agent and/or ATP-extraction agent. In embodiments in which a sample comprises cells, and intracellular ATP is desired for detection/quantification, reagents may be provided to lyse cells and/or liberate ATP from cells. In some embodiments, to free ATP sequestered within a cell and/or to lyse cells in a sample, cell lysing agents, such as non-ionic detergents, are included. Any cell lysing agent is contemplated including other non-ionic detergents, (e.g., Triton series detergents) cationic, anionic and zwitterionic detergents, bile salts, chaotropes, and any other agent that disrupts cellular membranes, including bacterial toxins such as oxylysins. Alternatively, any agent that allows for ATP extraction from a cell is contemplated (e.g., CTAB). Agents that allow for ATP extraction from a cell include detergents present at a concentration that permeablizes the cell membrane, allowing for ATP within the cell to leach into the surrounding media, but not present at such a concentration that produces a cell lysate.

In some embodiments, a kit or reagent composition comprises one or more stabilizing agents. In some embodiments, the stabilizing agent can be any compound that stabilizes the luciferase from degradation. Suitable stabilizing agents include proteins (e.g., bovine serum albumin, gelatin, etc.), detergents (e.g., non-ionic detergents, such as THESIT), etc.

In some embodiments, other agents may be included a kit or reagent composition herein. For example, a kit or reagent composition may include substances that are known to enhance the duration of luminescence resulting from a luciferase reaction, such as co-enzyme A (CoA), thiol reagents such as dithiothreitol, 13 mercaptoethanol, and metal ion chelators, such as EDTA, to prolong the signal, protease inhibitors, or salts (e.g., NaCl, KCl, $Na_2SO_4$, $NAHCO_3$, $NaH_2PO_4$, etc.).

In some embodiments, a reagent composition and/or other components of a kit are contained in one or more containers or vessels. In some embodiments, the components of a reagent composition are contained within a single container or vessel. In some embodiments, a kit may comprise multiple containers or vessels containing the reagent composition. In some embodiments, a kit comprises one or more containers or vessels containing reagents other than the reagent composition (see above). In some embodiments, components and reagents included in a kit are supplied in containers of any sort such that the life of the different components are preserved, and are not adsorbed or altered by the materials of the container. Containers or vessels may comprise or consist of any suitable material, such as glass, organic polymers, such as polycarbonate, polystyrene, etc., ceramic, metal or any other material typically employed to hold reagents. Examples of suitable containers include ampules, bottles, envelopes, test tubes, vials, flasks, bottles, syringes, or the like.

In some embodiments, kits comprise, and/or reagent compositions are provided with, appropriate instruction materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail. In some embodiments, the instructions instruct the user to combine reagent composition (e.g., comprising luciferase and luciferin) with a sample to detect or quantify ATP.

In some embodiments, a reagent composition is provided as a liquid reagent. In some embodiments, by providing a stable luciferase and luciferin in a single premixed liquid reagent, variability introduced by rehydrating a lyophilized reagent is eliminated. In other embodiments, a reagent composition is provided in lyophilized form. In some embodiments, other components of a kit herein may be provided as one or multiple liquid or dried compositions.

Although the luciferases and reagent compositions (e.g., comprising luciferase and luciferin) described herein are not limited to use in any particular method or application, due to their stability and activity in the presence of degradation products of luciferin, the luciferases and reagent compositions described herein are particularly useful for the detection of AT in a sample.

Because the luciferase-luciferin reaction is ATP-dependent, the luciferases and reagent compositions described herein find use in assays for to detect and/or quantify ATP. The luciferase-luciferin reaction allows ATP to be detected in a sample containing as little as $10^{-16}$ moles of ATP or less.

In some embodiments, provided herein are methods, compositions and kits that are used to effectively and accurately detect and quantify cellular ATP levels. In some embodiments, the luciferases and reagent compositions find use in the detection of ATP on surfaces, in non-cellular samples (e.g., water), for hygiene monitoring, etc.

In some embodiments, methods comprise the addition of a single reagent composition that comprises a luciferase and luciferin (and possibly dehydroluciferin) to a sample (e.g., a sample comprising or suspected of possibly comprising ATP) and detecting luminescence. In some embodiments, additional components and/or reagents (see above) are included with the reagent composition or added separately (e.g., a kinase inhibitor, a compound that prevents accumulation of ATP, a cell-lysing agent (e.g., a polyoxyethylene such as THESIT), an ATP extracting agent, magnesium, a buffer, salts, etc.). In some embodiments, the inclusion of the luciferase and luciferin in a single reagent speeds ATP detection, simplifies assays and handling, and increases reproducibility.

As addressed throughout, the methods, compositions and kits herein are particularly useful for the qualitative or quantitative detection of ATP (or ATP an analogue which can function as a luciferase substrate) in a sample. In some embodiments, a simple qualitative experiment in which luminescence is generated in a sample using a reagent composition (e.g., comprising luciferase and luciferin) indicates the presence of ATP. In some embodiments an assay is provided in which the amount of ATP in a sample is quantitated. ATP may be detected (e.g., qualitatively) and/or quantitated as a single time-point, at multiple time-points, or in real time using the luciferases, reagent compositions, and/or kits herein.

In some embodiments, a sample is anything that contains or is suspected of containing ATP or a suitable ATP analogue, such as cell lysates, intact cells, biopsies, foods, beverages, water, swabs wiped on surfaces such as those of animals, plants, or inanimate objects, and the like. Other examples of samples include compositions of a known ATP concentration. Cells or cell lysates may be from any organism, prokaryotic or eukaryotic. Eukaryotic cells may be from plants, animals, fungi, insects, etc. or cultured cells from such organisms. These examples are furnished only as examples and are not meant to be limiting.

A cell lysate comprises cellular components that are no longer organized into a recognizable intact cellular architecture. Cell lysates may have soluble and insoluble components, either of which may be removed before using the lysate. Lysates may be prepared by any means, including physical disruption using sonication, a dounce, mortar and pestle, freeze-thaw cycling, or any other device or process that destroys the physical integrity of cells; or lysis by detergents, such as those in which luciferase activity is maintained, such as zwitterionic and nonionic detergents, or cationic detergents DTAB or CTAB. Preferably, the cell lysate is produced in such a way that the integrity of the ATP concentration is preserved at the time the cells are harvested.

In some embodiments, to accurately detect ATP in a sample, enzymes that would degrade cellular ATP or those that would generate ATP are preferably inhibited or removed. Inhibitors of ATP-generating enzymes, those enzymes that have as a product or by-product ATP, such as the activity of kinases, may be incorporated into the reagent composition (e.g., comprising luciferase and luciferin) or into a kit comprising a reagent composition.

The luciferases, reagent compositions, methods, and kits herein permit a user to quantify the amount of ATP in a sample by quantifying the amount of luminescence. In some embodiments, the luciferase and luciferin (in a single composition) are applied to a test sample of interest. In some embodiments, the luciferase and luciferin (in a single composition) are also applied to a sample containing known amounts of ATP (control). The magnitude of the signal generated from the test sample correlates to the concentration of ATP in the sample. In some embodiments, the magnitude of the luminescent signal from the sample of unknown ATP concentration is correlated to signal generated either by internal controls (the addition of a known amount of ATP to a sample and measuring the subsequent luminescence) or external standard curves generated by measuring the luminescence of several samples of known ATP concentrations and plotting them graphically.

EXPERIMENTAL

Example 1

A library of random mutants was created using Diversify® PCR Random Mutagenesis Kit (Clonetech) and DNA from a thermal stable luciferase as a template. Mutant colonies were picked into 96-well plates and then grown for ~17 hours in LB media. The cultures were then diluted into LB induction media containing 0.02% rhamnose and 0.05% glucose. The induced cultures were then lysed and assayed with two assay reagents: Luciferin+ATP+detergent and Luciferin+ATP+detergent+dehydroluciferin. A ratio of the RLU values for each mutant was calculated (RLU+dehydroluciferin/RLU no dehydroluciferin), and samples that had the highest ratio were selected (FIG. 1). DNA from each of the mutants was isolated, pooled, and recombination mutagenesis was performed.

Figure 2:
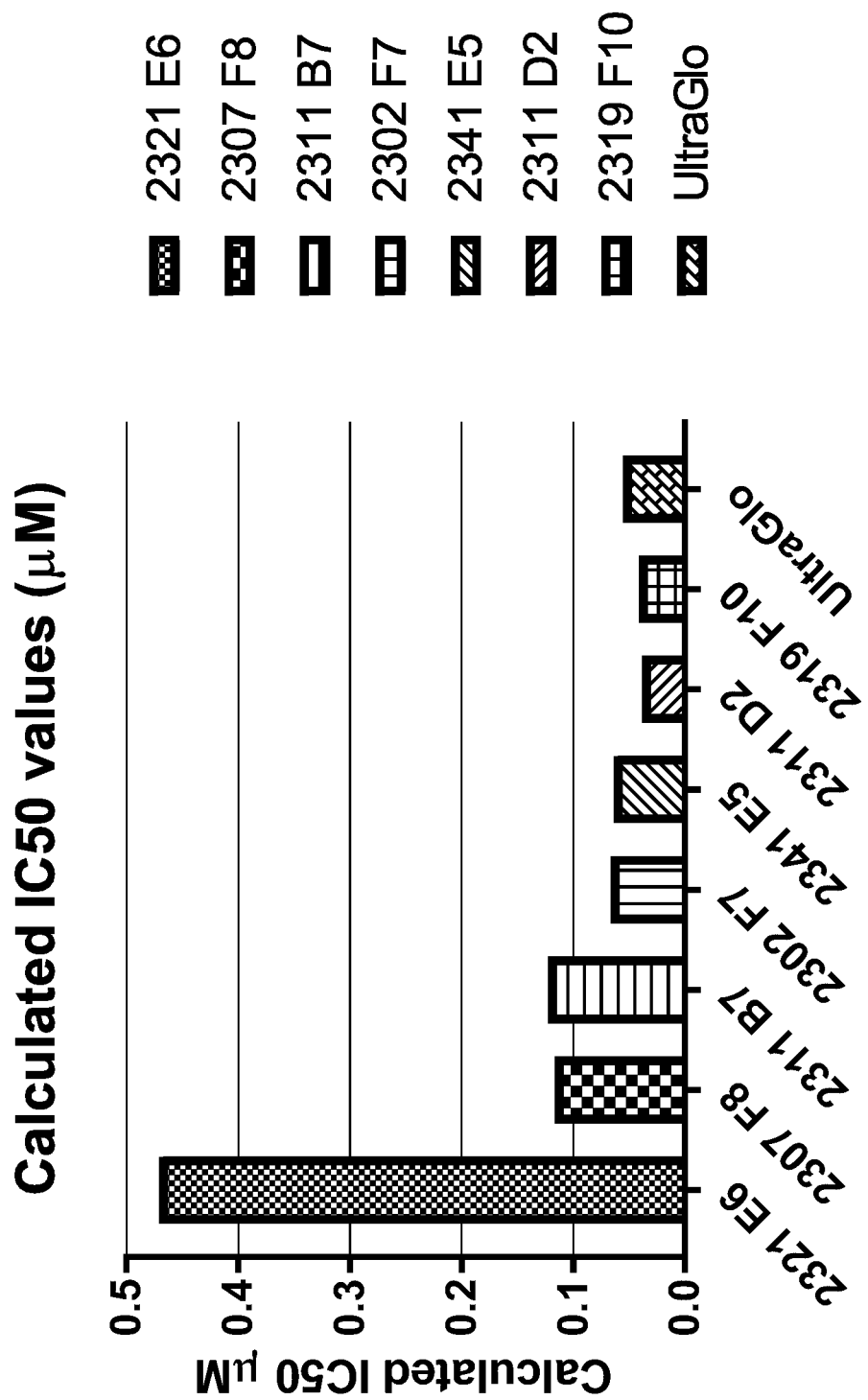
FIG. 2 shows a graph depicting calculated IC50 values for dehydroluciferin of variant luciferases and ULTRAGLO luciferase (Promega Corp., Madison, Wis.).

Select mutants in *E. coli* from the recombination mutagenesis were grown for secondary screening (same procedure as listed above), and then each mutant was combined with full detection reageant (Luciferin+detergent+ATP) containing varied amounts of dehydroluciferin. Samples were then measured using GloMax®-Multi+luminometer (Promega) IC50 values were calculated using GraphPad Prism log(inhibitor) vs. normalized response regression (FIG. 2).

Figure 3:
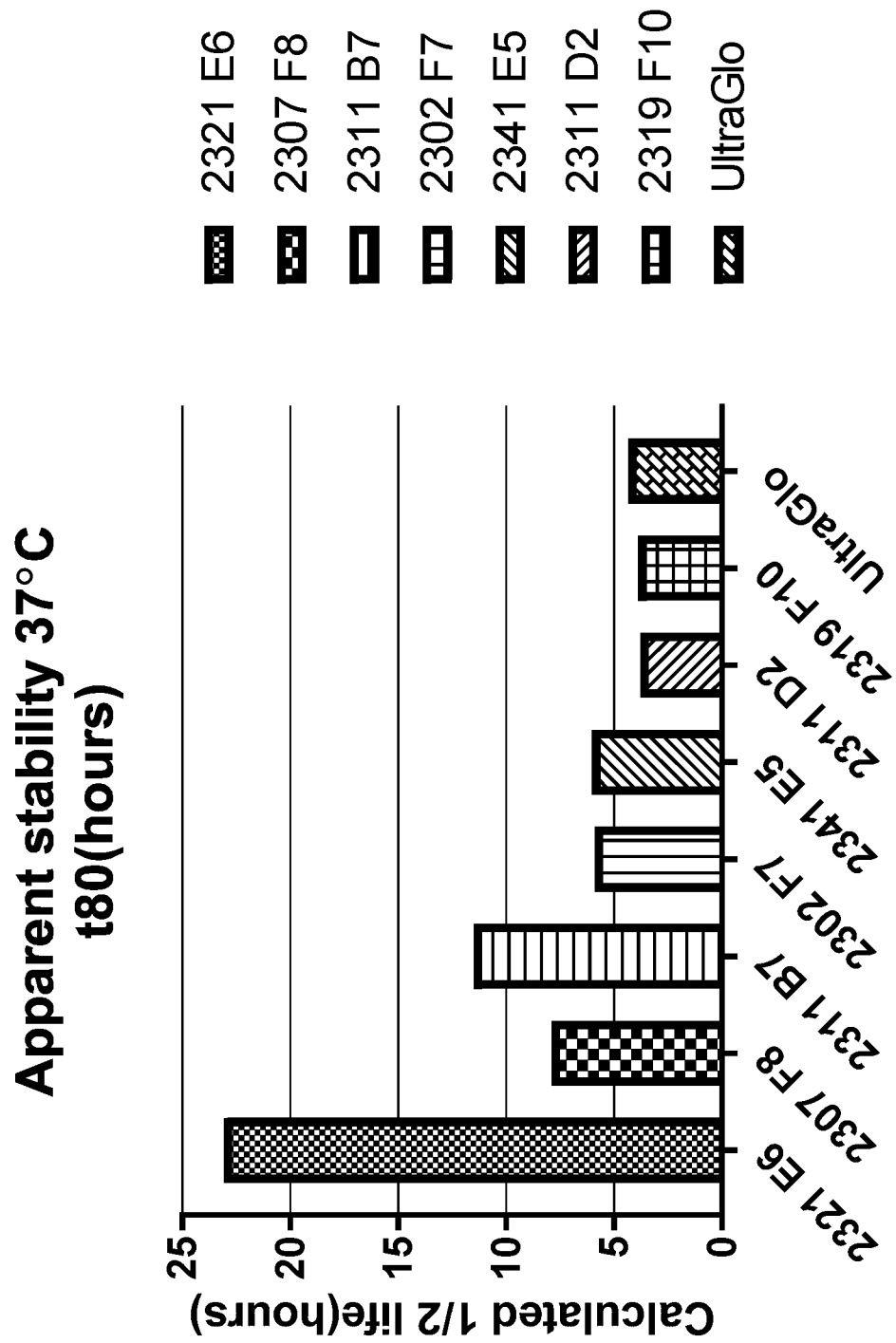
FIG. 3 shows a graph depicting the apparent stability of variant luciferases and ULTRAGLO luciferase (Promega Corp., Madison, Wis.).

Detection reagent (Luciferin in detergent) was prepared and then aliquots were incubated at 37° C. Aliquots were removed from 37° C. at various time-points and stored at 4° C. ATP was added to an aliquot of each of the detection reagent series, and then the detection reagent was combined with each of the lysed mutant luciferases. Luminescence was measured on a GloMax®-Multi+luminometer (Promega). An apparent stability was calculated using GraphPad Prism One phase decay regression (FIG. 3).

Example 2

Figure 4:
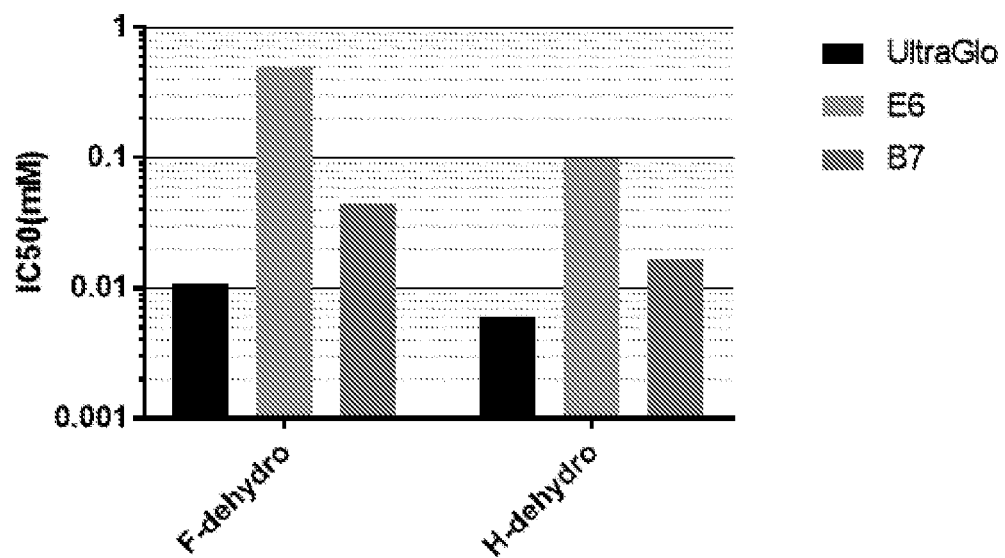
FIG. 4 shows RLU and IC50 values for exemplary enzymes.
Figure 4:
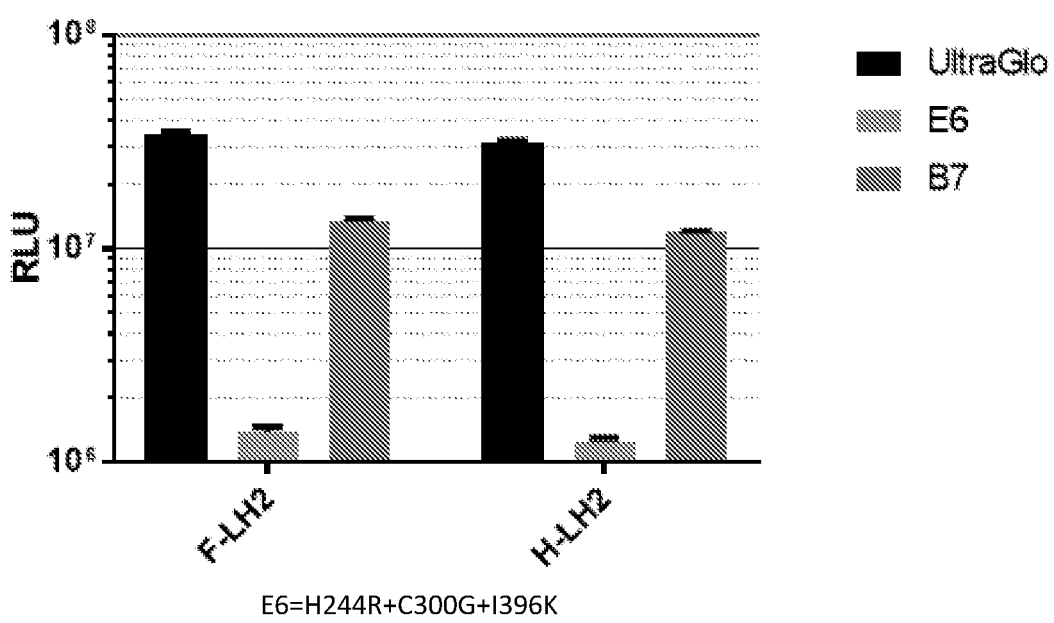

To determine RLU and IC50 values for the mutants described herein, two-4 mL solutions of E6, B7, and Ultra-Glo enzymes were prepared in Detection Reagent (1% Thesit, 0.1% DTAB, 0.08% CTAB, 0.2% Chlorohexidine digluconate, 100 mM MES pH 6.0, 5 mM MgCl2, 10 mM EGTA, 4 mM NaCitrate) containing 0.1% Prionex, 0.25 mM of either racemic F-LH2 or H-LH2 were added to the enzyme solutions. A 3× dilution series of F-dehydroluciferin and H-dehydroluciferin were prepared starting with 0.5 mM using the earlier prepared racemic luciferin mixtures as a diluent. 50 uL of each dehydroluciferin tiration series was then combined with 50 uL of 100 nM ATP. Samples were incubated for 1 minute, luminescence (RLU) was then measured using GloMax®-Multi+luminometer (Promega), and IC50 values for each enzyme (FIG. 4).

Example 3

Mutants E6 and B7 identified in the above recombination mutagenesis, as well as UltraGlo enzyme, were screened for their stability in the presence of breakdown products. Detection reagent+0.1% Prionex containing either racemic 0.25 mM H-LH2 or 0.25 mM F-LH2 was prepared. Eight, 2 mL aliquots were prepared for each substrate, and the samples incubated at 37° C. At various time points, the aliquots were transferred to 4° C.

Figure 5:
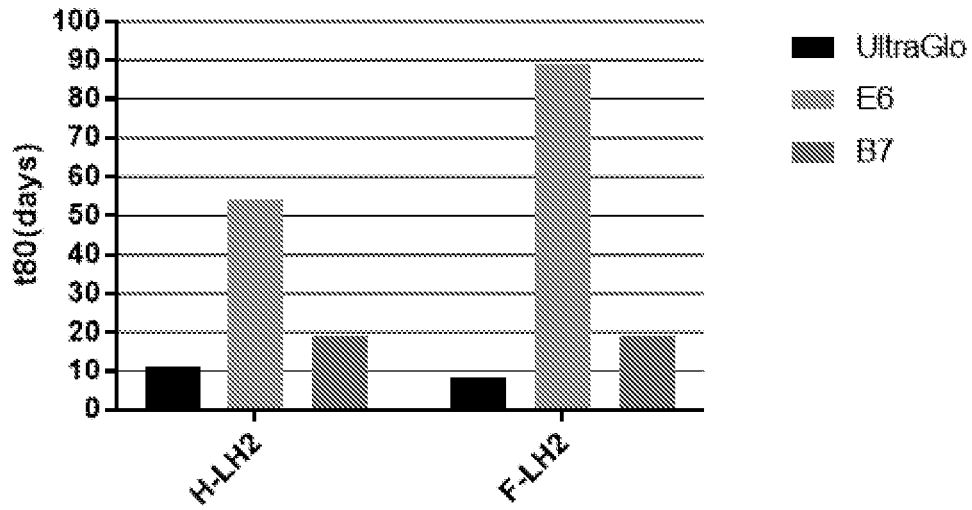
FIG. 5 shows the resistance and stability of exemplary mutants in the presence of complete reagent breakdown products.
Figure 5:
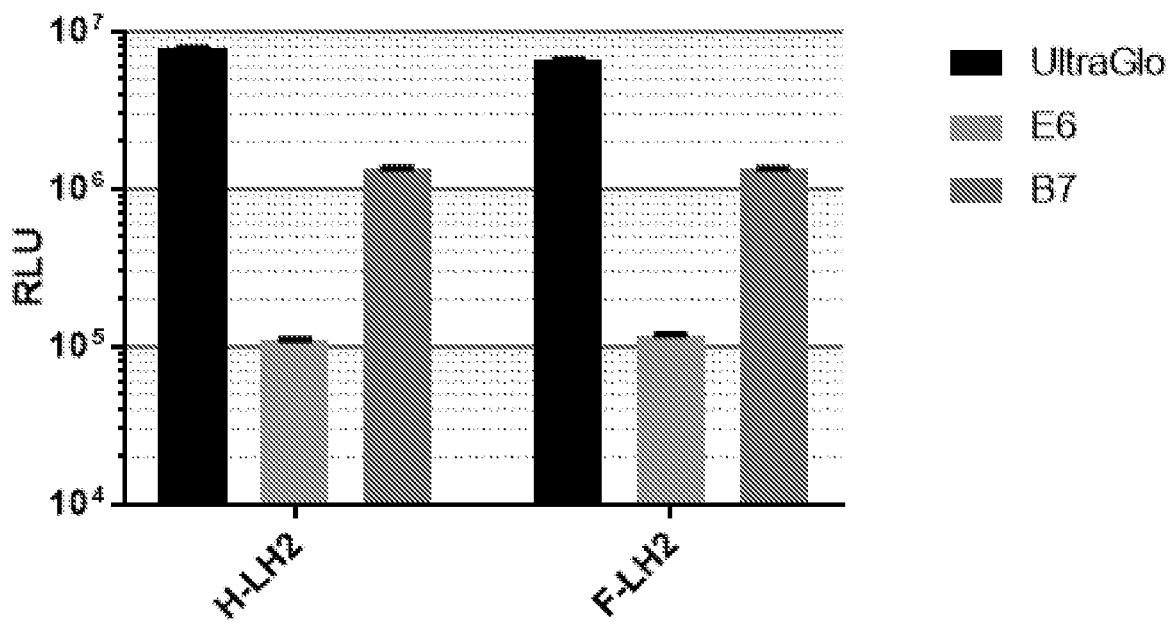

After all samples had been incubated and transferred, 500 uL of each sample was aliquoted in triplicate into wells of a 96-deep well plate. 0.01 mg/ml of each enzyme (UltraGlo, E6, or B7) was then added to each buffer aliquot. 50 uL of each substrate/enzyme solution was then combined with 50 uL 0.1 mM ATP. Samples were incubated for 3 minutes, and luminescence then measured using GloMax®-Multi+luminometer (Promega) (FIG. 5).

Example 4

To explore the inhibition of F-luciferin luminescence by dehydro-F-luciferin by combination mutants, the mutant Triple+300 (H244W, T344A, I396K, C300G) was screened for its resistance to dehydroluciferin.

Purified UltraGlo and Triple+300 luciferase enzymes were serially diluted from stocks in 1×TBS+1.0% Prionex to a concentration of 0.01 mg/ml. Racemic F-luciferin was serially diluted from stocks in water to 22 mM. Racemic dehydro-F-luciferin was serially diluted from stocks in water to 10 mM, and then 8 consecutive 4-fold serial dilutions were carried out for each concentration tested. ATP was diluted to 1 mM in BrightGlo Buffer or Detection Reagent buffer (depending on final reaction destination) to 1 mM concentration.

The following components were then combined into wells of a flat bottom, white, 96-well plate: 50 ul diluted ATP in buffer (BrightGlo or Detection Reagent; 0.5 mM final concentration), 50 ul diluted luciferase enzyme (0.05 mg/ml final concentration), 5 ul diluted F-luciferin (1 mM final concentration), and 4 ul diluted dehydro-F-luciferin (0.006-366.97 mM final concentration)

Reactions were incubated for 3 minutes at room temperature, and luminescence was measured using a GloMax Multi+plate reader. Data were analyzed in GraphPad Prism 7 using nonlinear regression by fitting the data to a Michaelis-Menten competitive inhibition enzyme kinetic model.

TABLE 1

|  | Ki (nM) | |
| --- | --- | --- |
|  | BrightGlo | Detection Reagent |
| UltraGlo | 39.9 | 419.7 |
| triple + 300 | 71.8 | 562.5 |

```
SEQUENCES
Wild-type firefly luciferase (protein)
                                              SEQ ID NO: 1
MEDAKNIKKGPAPFYPLEDGTAGEQLHKAMKRYALVPGTIAFTDAHIEVNITYAEYF

EMSVRLAEAMKRYGLNTNHRIVVCSENSLQFFMPVLGALFIGVAVAPANDIYNEREL

LNSMNISQPTVVFVSKKGLQKILNVQKKLPIIQKIIIMDSKTDYQGFQSMYTFVTSHLP

PGFNEYDFVPESFDRDKTIALIMNSSGSTGLPKGVALPHRTACVRFSHARDPIFGNQII

PDTAILSVVPFHHGFGMFTTLGYLICGFRVVLMYRFEEELFLRSLQDYKIQSALLVPT

LFSFFAKSTLIDKYDLSNLHEIASGGAPLSKEVGEAVAKRFHLPGIRQGYGLTETTSAI

LITPEGDDKPGAVGKVVPFFEAKVVDLDTGKTLGVNQRGELCVRGPMIMSGYVNNP

EATNALIDKDGWLHSGDIAYWDEDEHFFIVDRLKSLIKYKGYQVAPAELESILLQHP

NIFDAGVAGLPDDDAGELPAAVVVLEHGKTMTEKEIVDYVASQVTTAKKLRGGVVF

VDEVPKGLTGKLDARKIREILIKAKKGGKSKL

Wild-type firefly luciferase (nucleotide)
                                              SEQ ID NO: 2
CTGCAGAAATAACTAGGTACTAAGCCCGTTTGTGAAAAGTGGCCAAACCCATAA

ATTTGGCAATTACAATAAAGAAGCTAAAATTGTGGTCAAACTCACAAACATTTTT

ATTATATACATTTTAGTAGCTGATGCTTATAAAAGCAATATTTAAATCGTAAACA

ACAAATAAAATAAAATTTAAACGATGTGATTAAGAGCCAAAGGTCCTCTAGAAA

AAGGTATTTAAGCAACGGAATTCCTTTGTGTTACATTCTTGAATGTCGCTCGCAG

TGACATTAGCATTCCGGTACTGTTGGTAAAATGGAAGACGCCAAAAACATAAAG

AAAGGCCCGGCGCCATTCTATCCTCTAGAGGATGGAACCGCTGGAGAGCAACTG

CATAAGGCTATGAAGAGATACGCCCTGGTTCCTGGAACAATTGCTTTTGTGAGTA

TTTCTGTCTGATTTCTTTCGAGTTAACGAAATGTTCTTATGTTTCTTTAGACAGAT
```

-continued

```
GCACATATCGAGGTGAACATCACGTACGCGGAATACTTCGAAATGTCCGTTCGGT

TGGCAGAAGCTATGAAACGATATGGGCTGAATACAAATCACAGAATCGTCGTAT

GCAGTGAAAACTCTCTTCAATTCTTTATGCCGGTGTTGGGCGCGTTATTTATCGGA

GTTGCAGTTGCGCCCGCGAACGACATTTATAATGAACGTAAGCACCCTCGCCATC

AGACCAAAGGGAATGACGTATTTAATTTTTAAGGTGAATTGCTCAACAGTATGAA

CATTTCGCAGCCTACCGTAGTGTTTGTTTCCAAAAAGGGGTTGCAAAAAATTTTG

AACGTGCAAAAAAAATTACCAATAATCCAGAAAATTATTATCATGGATTCTAAA

ACGGATTACCAGGGATTTCAGTCGATGTACACGTTCGTCACATCTCATCTACCTC

CCGGTTTTAATGAATACGATTTTGTACCAGAGTCCTTTGATCGTGACAAAACAAT

TGCACTGATAATGAATTCCTCTGGATCTACTGGGTTACCTAAGGGTGTGGCCCTT

CCGCATAGAACTGCCTGCGTCAGATTCTCGCATGCCAGGTATGTCGTATAACAAG

AGATTAAGTAATGTTGCTACACACATTGTAGAGATCCTATTTTTGGCAATCAAAT

CATTCCGGATACTGCGATTTTAAGTGTTGTTCCATTCCATCACGGTTTTGGAATGT

TTACTACACTCGGATATTTGATATGTGGATTTCGAGTCGTCTTAATGTATAGATTT

GAAGAAGAGCTGTTTTTACGATCCCTTCAGGATTACAAAATTCAAAGTGCGTTGC

TAGTACCAACCCTATTTTCATTCTTCGCCAAAAGCACTCTGATTGACAAATACGA

TTTATCTAATTTACACGAAATTGCTTCTGGGGCGCACCTCTTTCGAAAGAAGTC

GGGGAAGCGGTTGCAAAACGGTGAGTTAAGCGCATTGCTAGTATTTCAAGGCTC

TAAAACGGCGCGTAGCTTCCATCTTCCAGGGATACGACAAGGATATGGGCTCACT

GAGACTACATCAGCTATTCTGATTACACCCGAGGGGGATGATAAACCGGGCGCG

GTCGGTAAAGTTGTTCCATTTTTTGAAGCGAAGGTTGTGGATCTGGATACCGGGA

AAACGCTGGGCGTTAATCAGAGAGGCGAATTATGTGTCAGAGGACCTATGATTA

TGTCCGGTTATGTAAACAATCCGGAAGCGACCAACGCCTTGATTGACAAGGATG

GATGGCTACATTCTGGAGACATAGCTTACTGGGACGAAGACGAACACTTCTTCAT

AGTTGACCGCTTGAAGTCTTTAATTAAATACAAAGGATATCAGGTAATGAAGATT

TTTACATGCACACACGCTACAATACCTGTAGGTGGCCCCCGCTGAATTGGAATCG

ATATTGTTACAACACCCCAACATCTTCGACGCGGGCGTGGCAGGTCTTCCCGACG

ATGACGCCGGTGAACTTCCCGCCGCCGTTGTTGTTTTGGAGCACGGAAAGACGAT

GACGGAAAAAGAGATCGTGGATTACGTCGCCAGTAAATGAATTCGTTTTACGTTA

CTCGTACTACAATTCTTTTCATAGGTCAAGTAACAACCGCGAAAAAGTTGCGCGG

AGGAGTTGTGTTTGTGGACGAAGTACCGAAAGGTCTTACCGGAAAACTCGACGC

AAGAAAAATCAGAGAGATCCTCATAAAGGCCAAGAAGGGCGGAAAGTCCAAAT

TGTAAAATGTAACTGTATTCAGCGATGACGAAATTCTTAGCTATTGTAATATTAT

ATGCAAATTGATGAATGGTAATTTTGTAATTGTGGGTCACTGTACTATTTTAACG

AATAATAAAATCAGGTATAGGTAACTAAAAA
```

ULTRA GLO luciferase (protein)

SEQ ID NO: 3

```
MADKNILYGPEPFYPLEDGTAGEQMFDALSRYAAIPGCIALTNAHTKENVLYEEFLK

LSCRLAESFKKYGLKQNDTIAVCSENSLQFFLPVIASLYLGIIVAPVNDKYIERELIHSL

GIVKPRIVFCSKNTFQKVLNVKSKLKSIETIIILDLNEDLGGYQCLNNFISQNSDSNLDV

KKFKPYSFNRDDQVASIMFSSGTTGLPKGVMLTHKNIVARFSIAKDPTFGNAINPTSA
```

-continued

ILTVIPFHHGFGMMTTLGYFTCGFRVVLMHTFEEKLFLQSLQDYKVESTLLVPTLMA

FLAKSALCEKYDLSHLKEIASGGAPLSKEIGEMVKKRFKLNFVRQGYGLTETTSAVLI

TPKGDAKPGSTGKIVPLHAVKVVDPTTGKILGPNEPGELYFKGPMIMKGYYNNEEAT

KAIIDNDGWLRSGDIAYYDNDGHFYIVDRLKSLIKYKGYQVAPAEIEGILLQHPYIVD

AGVTGIPDEAAGELPAAGVVVQTGKYLNEQIVQDYVASQVSTAKWLRGGVKFLDEI

PKGSTGKIDRKVLRQMLEKHTNGHHHHHHHH*

ULTRA GLO luciferase (nucleic acid)
SEQ ID NO: 4
ATGGCTGACAAAAACATCCTGTATGGTCCGGAACCGTTCTACCCACTGGAAGATG

GTACCGCTGGTGAACAGATGTTTGACGCATTATCTCGTTATGCAGCTATTCCGGG

CTGCATAGCATTGACAAATGCTCATACAAAAGAAAATGTTTTATATGAAGAGTTT

CTGAAACTGTCGTGTCGTTTAGCGGAAAGTTTTAAAAAGTATGGATTAAAACAAA

ACGACACAATAGCGGTGTGTAGCGAAAATAGTCTGCAATTTTTCCTTCCTGTAAT

TGCATCATTGTATCTTGGAATAATTGTGGCACCTGTTAACGATAAATACATTGAA

CGTGAATTAATACACAGTCTTGGTATTGTAAAACCACGCATAGTTTTTTGCTCCA

AGAATACTTTTCAAAAAGTACTGAATGTAAAATCTAAATTAAAATCTATTGAAAC

TATTATTATATTAGACTTAAATGAAGACTTAGGAGGTTATCAATGCCTCAACAAC

TTTATTTCTCAAAATTCCGATAGTAATCTGGACGTAAAAAAATTTAAACCCTATT

CTTTTAATCGAGACGATCAGGTTGCGTCGATTATGTTTTCTTCTGGTACAACTGGT

CTGCCGAAGGGAGTCATGCTAACTCACAAGAATATTGTTGCACGATTTTCTATTG

CAAAAGATCCTACTTTTGGTAACGCAATTAATCCCACGTCAGCAATTTTAACGGT

AATACCTTTCCACCATGGTTTTGGTATGATGACCACATTAGGATACTTTACTTGTG

GATTCCGAGTTGTTCTAATGCACACGTTTGAAGAAAAACTATTTCTACAATCATT

ACAAGATTATAAAGTGGAAAGTACTTTACTTGTACCAACATTAATGGCATTTCTT

GCAAAAAGTGCATTAGTTGAAAAGTACGATTTATCGCACTTAAAAGAAATTGCA

TCTGGTGGCGCACCTTTATCAAAAGAAATTGGGGAGATGGTGAAAAAACGGTTT

AAATTAAACTTTGTCAGGCAAGGGTATGGATTAACAGAAACCACTTCGGCTGTTT

TAATTACACCGAAAGGTGACGCCAAACCGGGATCAACTGGTAAAATAGTACCAT

TACACGCTGTTAAAGTTGTCGATCCTACAACAGGAAAAATTTTGGGGCCAAATGA

ACCTGGAGAATTGTATTTTAAAGGCCCGATGATAATGAAGGGTTATTATAATAAT

GAAGAAGCTACTAAAGCAATTATTGATAATGACGGATGGTTGCGCTCTGGTGAT

ATTGCTTATTATGACAATGATGGCCATTTTTATATTGTGGACAGGCTGAAGTCAC

TGATTAAATATAAAGGTTATCAGGTTGCACCTGCTGAAATTGAGGGAATACTCTT

ACAACATCCGTATATTGTTGATGCCGGCGTTACTGGTATACCGGATGAAGCCGCG

GGCGAGCTTCCAGCTGCAGGTGTTGTAGTACAGACTGGAAAATATCTAAACGAA

CAAATCGTACAAGATTATGTTGCCAGTCAAGTTTCAACAGCCAAATGGCTACGTG

GTGGGGTGAAATTTTTGGATGAAATTCCCAAAGGATCAACTGGAAAAATTGACA

GAAAAGTGTTAAGACAAATGTTAGAAAAACACACCAATGGGCATCACCATCACC

ACCATCATCACTAA

E6 luciferase mutant (protein)
SEQ ID NO: 5
MADKNILYGPEPFYPLEDGTAGEQMFDALSRYAAIPGCIALTNAHTKENVLYEEFLK

LSCRLAESFKKYGLKQNDTIAVCSENSLQFFLPVIASLYLGIIVAPVNDKYIERELIHSL

-continued

GIVKPRIVFCSKNTFQKVLNVKSKLKSIETIIILDLNEDLGGYQCLNNFISQNSDSNLDV

KKFKPYSFNRDDQVASIMFSSGTTGLPKGVMLTHKNIVARFSIAKDPTFGNAINPTSA

ILTVIPFHRGFGMMTTLGYFTCGFRVVLMHTFEEKLFLQSLQDYKVESTLLVPTLMA

FLAKSALGEKYDLSHLKEIASGGAPLSKEIGEMVKKRFKLNFVRQGYGLTETTSAVLI

TPKGDAKPGSTGKIVPLHAVKVVDPTTGKILGPNEPGELYFKGPMKMKGYYNNEEA

TKAIIDNDGWLRSGDIAYYDNDGHFYIVDRLKSLIKYKGYQVAPAEIEGILLQHPYIV

DAGVTGIPDEAAGELPAAGVVVQTGKYLNEQIVQDYVASQVSTAKWLRGGVKFLD

EIPKGSTGKIDRKVLRQMLEKHTNGHHHHHHHH* luciferase mutant (nucleic acid)

SEQ ID NO: 6

ATGGCTGACAAAAACATCCTGTATGGTCCGGAACCGTTCTACCCACTGGAAGATG

GTACCGCTGGTGAACAGATGTTTGACGCATTATCTCGTTATGCAGCTATTCCGGG

CTGCATAGCATTGACAAATGCTCATACAAAAGAAAATGTTTTATATGAAGAGTTT

CTGAAACTGTCGTGTCGTTTAGCGGAAAGTTTTAAAAAGTATGGATTAAAACAAA

ATGACACAATAGCGGTGTGTAGCGAAAATAGTCTGCAATTTTTCCTTCCTGTAAT

TGCATCATTGTATCTTGGAATAATTGTGGCACCTGTTAACGATAAATACATTGAA

CGTGAATTAATACACAGTCTTGGTATTGTAAAACCACGCATAGTTTTTTGCTCCA

AGAATACTTTTCAAAAAGTACTGAATGTAAAATCTAAATTAAAATCTATTGAAAC

TATTATTATATTAGACTTAAATGAAGACTTAGGAGGTTATCAATGCCTCAACAAC

TTTATTTCTCAAAATTCCGATAGTAATCTGGACGTAAAAAAATTTAAACCCTATT

CTTTTAATCGAGACGATCAGGTTGCGTCGATTATGTTTTCTTCTGGTACAACTGGT

CTGCCGAAGGGAGTCATGCTAACTCACAAGAATATTGTTGCACGATTTTCTATTG

CAAAAGATCCTACTTTTGGTAACGCAATTAATCCCACGTCAGCAATTTTAACGGT

AATACCTTTCCACCGTGGTTTTGGTATGATGACCACATTAGGATACTTTACTTGTG

GATTCCGAGTTGTTCTAATGCACACGTTTGAAGAAAAACTATTTCTACAATCATT

ACAAGATTATAAAGTGGAAAGTACTTTACTTGTACCAACATTAATGGCATTTCTT

GCAAAAAGTGCATTAGGTGAAAAGTACGATTTATCGCACTTAAAAGAAATTGCA

TCTGGTGGCGCACCTTTATCAAAAGAAATTGGGGAGATGGTGAAAAAACGGTTT

AAATTAAACTTTGTCAGGCAAGGGTATGGATTAACAGAAACCACTTCGGCTGTTT

TAATTACACCGAAAGGTGACGCCAAACCGGGATCAACTGGTAAAATAGTACCAT

TACACGCTGTTAAAGTTGTCGATCCTACAACAGGAAAAATTTTGGGGCCAAATGA

ACCTGGAGAATTGTATTTTAAAGGCCCGATGAAAATGAAGGGTTATTATAATAAT

GAAGAAGCTACTAAAGCAATTATTGATAATGACGGATGGTTGCGCTCTGGTGAT

ATTGCTTATTATGACAATGATGGCCATTTTTATATTGTGGACAGGCTGAAGTCAC

TGATTAAATATAAAGGTTATCAGGTTGCACCTGCTGAAATTGAGGGAATACTCTT

ACAACATCCGTATATTGTTGATGCCGGCGTTACTGGTATACCGGATGAAGCCGCG

GGCGAGCTTCCAGCTGCAGGTGTTGTAGTACAGACTGGAAAATATCTAAACGAA

CAAATCGTACAAGATTATGTTGCCAGTCAAGTTTCAACAGCCAAATGGCTACGTG

GTGGGGTGAAATTTTTGGATGAAATTCCCAAAGGATCAACTGGAAAAATTGACA

GAAAAGTGTTAAGACAAATGTTAGAAAAACACACCAATGGGCATCACCATCACC

ACCATCATCACTAAT

-continued

B7 luciferase mutant (protein)
SEQ ID NO: 7

MADKNILYGPEPFYPLEDGTAGEQMFDALSRYAAIPGCIALTNAHTKENVLYEEFLK

LSCRLAESFKKYGLKQNDTIAVCSENSLQFFLPVIASLYLGIIVAPVNDKYIERELIHSL

GIVKPRIVFCSKNTFQKVLNVKSKLKSIETIIILDLNEDLGGYQCLNNFISQNSDSNLDV

KKFKPYSFNRDDQVASIMFSSGTTGLPKGVMLTHKNIVARFSIAKDPTFGNAINPTSA

ILTVLPFHHGFGMMTTLGSFTCGFRVVLMHTFEEKLFLQSLQDYKVESTLLVPTLMA

FLAKSALVEKYDLSHLKEIASGGAPLSKEIGEMVKKRFKLNFVRQGYGLTEATSAVLI

TPKGDAKPGSTGKIVPLHAVKVVDPTTGKILGPNEPGELYFKGPMKMKGYYNNEEA

TKAIIDNDGWLRSGDIAYYDNDGHFYIVDRLKSLIKYKGYQVAPAEIEGILLQHPYIV

DAGVTGIPDEAAGELPAAGVVVQTGKYLNEQIVQDYVASQVSTAKWLRGGVKFLD

EIPKGSTGKIDRKVLRQMLEKHTNGHHHHHHHH*

B7 luciferase mutant (nucleic acid)
SEQ ID NO: 8

ATGGCTGACAAAAACATCCTGTATGGTCCGGAACCGTTCTACCCACTGGAAGATG

GTACCGCTGGTGAACAGATGTTTGACGCATTATCTCGTTATGCAGCTATTCCGGG

CTGCATAGCATTGACAAATGCTCATACAAAAGAAAATGTTTTATATGAAGAGTTT

CTGAAACTGTCGTGTCGTTTAGCGGAAAGTTTTAAAAAGTATGGATTAAAACAAA

ACGACACAATAGCGGTGTGTAGCGAAAATAGTCTGCAATTTTTCCTTCCTGTAAT

TGCATCATTGTATCTTGGAATAATTGTGGCACCTGTTAACGATAAATACATTGAA

CGTGAATTAATACACAGTCTTGGTATTGTAAAACCACGCATAGTTTTTTGCTCCA

AGAATACTTTTCAAAAAGTACTGAATGTAAAATCTAAATTAAAATCTATTGAAAC

TATTATTATATTAGACTTAAATGAAGACTTAGGAGGTTATCAATGCCTCAACAAC

TTTATTTCTCAAAATTCCGATAGTAATCTGGACGTAAAAAAATTTAAACCCTATT

CTTTTAATCGAGACGATCAGGTTGCGTCGATTATGTTTCTTCTGGTACAACTGGT

CTGCCGAAGGGAGTCATGCTAACTCACAAGAATATTGTTGCACGATTTTCTATTG

CAAAAGATCCTACTTTTGGTAACGCAATTAATCCCACGTCAGCAATTTTAACGGT

ATTACCTTTCCACCATGGTTTTGGTATGATGACCACATTAGGATCCTTTACTTGTG

GATTCCGAGTTGTTCTAATGCACACGTTTGAAGAAAAACTATTTCTACAATCATT

ACAAGATTATAAAGTGGAAAGTACTTTACTTGTACCAACATTAATGGCATTTCTT

GCAAAAAGTGCATTAGTTGAAAAGTACGATTTATCGCACTTAAAAGAAATTGCA

TCTGGTGGCGCACCTTTATCAAAAGAAATTGGGGAGATGGTGAAAAAACGGTTT

AAATTAAACTTTGTCAGGCAAGGGTATGGATTAACAGAAGCCACTTCGGCTGTTT

TAATTACACCGAAAGGTGACGCCAAACCGGGATCAACTGGTAAAATAGTACCAT

TACACGCTGTTAAAGTTGTCGATCCTACAACAGGAAAAATTTTGGGGCCAAATGA

ACCTGGAGAATTGTATTTTAAAGGCCCGATGAAAATGAAGGGTTATTATAATAAT

GAAGAAGCTACTAAAGCAATTATTGATAATGACGGATGGTTGCGCTCTGGTGAT

ATTGCTTATTATGACAATGATGGCCATTTTTATATTGTGGACAGGCTGAAGTCAC

TGATTAAATATAAAGGTTATCAGGTTGCACCTGCTGAAATTGAGGGAATACTCTT

ACAACATCCGTATATTGTTGATGCCGGCGTTACTGGTATACCGGATGAAGCCGCG

GGCGAGCTTCCAGCTGCAGGTGTTGTAGTACAGACTGGAAAATATCTAAACGAA

CAAATCGTACAAGATTATGTTGCCAGTCAAGTTTCAACAGCCAAATGGCTACGTG

GTGGGGTGAAATTTTTGGATGAAATTCCCAAAGGATCAACTGGAAAAATTGACA

-continued

GAAAAGTGTTAAGACAAATGTTAGAAAAACACACCAATGGGCATCACCATCACC

ACCATCATCACTAA

UltraGlo Triple mutant (H244W + T344A + I396K)
(amino acid)
SEQ ID NO: 9
MADKNILYGPEPFYPLEDGTAGEQMFDALSRYAAIPGCIALTNAHTKENVLYEEFLK

LSCRLAESFKKYGLKQNDTIAVCSENSLQFFLPVIASLYLGIIVAPVNDKYIERELIHSL

GIVKPRIVFCSKNTFQKVLNVKSKLKSIETIIILDLNEDLGGYQCLNNFISQNSDSNLDV

KKFKPYSFNRDDQVASIMFSSGTTGLPKGVMLTHKNIVARFSIAKDPTFGNAINPTSA

ILTVIPFHWGFGMMTTLGYFTCGFRVVLMHTFEEKLFLQSLQDYKVESTLLVPTLMA

FLAKSALVEKYDLSHLKEIASGGAPLSKEIGEMVKKRFKLNFVRQGYGLTEATSAVLI

TPKGDAKPGSTGKIVPLHAVKVVDPTTGKILGPNEPGELYFKGPMKMKGYYNNEEA

TKAIIDNDGWLRSGDIAYYDNDGHFYIVDRLKSLIKYKGYQVAPAEIEGILLQHPYIV

DAGVTGIPDEAAGELPAAGVVVQTGKYLNEQIVQDYVASQVSTAKWLRGGVKFLD

EIPKGSTGKIDRKVLRQMLEKHTNGHHHHHHHH

UltraGlo Triple mutant (H244W + T344A + I396K)
(nucleic acid)
SEQ ID NO: 10
ATGGCTGACAAAAACATCCTGTATGGTCCGGAACCGTTCTACCCACTGGAAGATG

GTACCGCTGGTGAACAGATGTTTGACGCATTATCTCGTTATGCAGCTATTCCGGG

CTGCATAGCATTGACAAATGCTCATACAAAAGAAAATGTTTTATATGAAGAGTTT

CTGAAACTGTCGTGTCGTTTAGCGGAAAGTTTTAAAAAGTATGGATTAAAACAAA

ACGACACAATAGCGGTGTGTAGCGAAAATAGTCTGCAATTTTTCCTTCCTGTAAT

TGCATCATTGTATCTTGGAATAATTGTGGCACCTGTTAACGATAAATACATTGAA

CGTGAATTAATACACAGTCTTGGTATTGTAAAACCACGCATAGTTTTTTGCTCCA

AGAATACTTTTCAAAAAGTACTGAATGTAAAATCTAAATTAAAATCTATTGAAAC

TATTATTATATTAGACTTAAATGAAGACTTAGGAGGTTATCAATGCCTCAACAAC

TTTATTTCTCAAAATTCCGATAGTAATCTGGACGTAAAAAAATTTAAACCCTATT

CTTTTAATCGAGACGATCAGGTTGCGTCGATTATGTTTTCTTCTGGTACAACTGGT

CTGCCGAAGGGAGTCATGCTAACTCACAAGAATATTGTTGCACGATTTTCTATTG

CAAAAGATCCTACTTTTGGTAACGCAATTAATCCCACGTCAGCAATTTTAACGGT

AATACCTTTCCACTGGGGTTTTGGTATGATGACCACATTAGGATACTTTACTTGTG

GATTCCGAGTTGTTCTAATGCACACGTTTGAAGAAAAACTATTTCTACAATCATT

ACAAGATTATAAAGTGGAAAGTACTTTACTTGTACCAACATTAATGGCATTTCTT

GCAAAAAGTGCATTAGTTGAAAAGTACGATTTATCGCACTTAAAAGAAATTGCA

TCTGGTGGCGCACCTTTATCAAAAGAAATTGGGGAGATGGTGAAAAAACGGTTT

AAATTAAACTTTGTCAGGCAAGGGTATGGATTAACAGAAGCCACTTCGGCTGTTT

TAATTACACCGAAAGGTGACGCCAAACCGGGATCAACTGGTAAAATAGTACCAT

TACACGCTGTTAAAGTTGTCGATCCTACAACAGGAAAAATTTTGGGGCCAAATGA

ACCTGGAGAATTGTATTTTAAAGGCCCGATGAAAATGAAGGGTTATTATAATAAT

GAAGAAGCTACTAAAGCAATTATTGATAATGACGGATGGTTGCGCTCTGGTGAT

ATTGCTTATTATGACAATGATGGCCATTTTTATATTGTGGACAGGCTGAAGTCAC

TGATTAAATATAAAGGTTATCAGGTTGCACCTGCTGAAATTGAGGGAATACTCTT

-continued

```
ACAACATCCGTATATTGTTGATGCCGGCGTTACTGGTATACCGGATGAAGCCGCG

GGCGAGCTTCCAGCTGCAGGTGTTGTAGTACAGACTGGAAAATATCTAAACGAA

CAAATCGTACAAGATTATGTTGCCAGTCAAGTTTCAACAGCCAAATGGCTACGTG

GTGGGGTGAAATTTTTGGATGAAATTCCCAAAGGATCAACTGGAAAAATTGACA

GAAAAGTGTTAAGACAAATGTTAGAAAAACACACCAATGGGCATCACCATCACC

ACCATCATCACTAA
```

UltraGlo Triple + 300 (H244W + T344A + I396K + C300G)
(amino acid)
SEQ ID NO: 11

```
MADKNILYGPEPFYPLEDGTAGEQMFDALSRYAAIPGCIALTNAHTKENVLYEEFLK

LSCRLAESFKKYGLKQNDTIAVCSENSLQFFLPVIASLYLGIIVAPVNDKYIERELIHSL

GIVKPRIVFCSKNTFQKVLNVKSKLKSIETIIILDLNEDLGGYQCLNNFISQNSDSNLDV

KKFKPYSFNRDDQVASIMFSSGTTGLPKGVMLTHKNIVARFSIAKDPTFGNAINPTSA

ILTVIPFHWGFGMMTTLGYFTCGFRVVLMHTFEEKLFLQSLQDYKVESTLLVPTLMA

FLAKSALGEKYDLSHLKEIASGGAPLSKEIGEMVKKRFKLNFVRQGYGLTEATSAVLI

TPKGDAKPGSTGKIVPLHAVKVVDPTTGKILGPNEPGELYFKGPMKMKGYYNNEEA

TKAIIDNDGWLRSGDIAYYDNDGHFYIVDRLKSLIKYKGYQVAPAEIEGILLQHPYIV

DAGVTGIPDEAAGELPAAGVVVQTGKYLNEQIVQDYVASQVSTAKWLRGGVKFLD

EIPKGSTGKIDRKVLRQMLEKHTNGHHHHHHHH
```

UltraGlo Triple + 300 (H244W + T344A + I396K + C300G)
(nucleic acid)
SEQ ID NO: 12

```
ATGGCTGACAAAAACATCCTGTATGGTCCGGAACCGTTCTACCCACTGGAAGATG

GTACCGCTGGTGAACAGATGTTTGACGCATTATCTCGTTATGCAGCTATTCCGGG

CTGCATAGCATTGACAAATGCTCATACAAAAGAAAATGTTTTATATGAAGAGTTT

CTGAAACTGTCGTGTCGTTTAGCGGAAAGTTTTAAAAAGTATGGATTAAAACAAA

ACGACACAATAGCGGTGTGTAGCGAAAATAGTCTGCAATTTTTCCTTCCTGTAAT

TGCATCATTGTATCTTGGAATAATTGTGGCACCTGTTAACGATAAATACATTGAA

CGTGAATTAATACACAGTCTTGGTATTGTAAAACCACGCATAGTTTTTTGCTCCA

AGAATACTTTTCAAAAAGTACTGAATGTAAAATCTAAATTAAAATCTATTGAAAC

TATTATTATATTAGACTTAAATGAAGACTTAGGAGGTTATCAATGCCTCAACAAC

TTTATTTCTCAAAATTCCGATAGTAATCTGGACGTAAAAAAATTTAAACCCTATT

CTTTTAATCGAGACGATCAGGTTGCGTCGATTATGTTTTCTTCTGGTACAACTGGT

CTGCCGAAGGGAGTCATGCTAACTCACAAGAATATTGTTGCACGATTTTCTATTG

CAAAAGATCCTACTTTTGGTAACGCAATTAATCCCACGTCAGCAATTTTAACGGT

AATACCTTTCCACTGGGGTTTTGGTATGATGACCACATTAGGATACTTTACTTGTG

GATTCCGAGTTGTTCTAATGCACACGTTTGAAGAAAAACTATTTCTACAATCATT

ACAAGATTATAAAGTGGAAAGTACTTTACTTGTACCAACATTAATGGCATTTCTT

GCAAAAAGTGCATTAGGTGAAAAGTACGATTTATCGCACTTAAAAGAAATTGCA

TCTGGTGGCGCACCTTTATCAAAAGAAATTGGGGAGATGGTGAAAAAACGGTTT

AAATTAAACTTTGTCAGGCAAGGGTATGGATTAACAGAAGCCACTTCGGCTGTTT

TAATTACACCGAAAGGTGACGCCAAACCGGGATCAACTGGTAAAATAGTACCAT

TACACGCTGTTAAAGTTGTCGATCCTACAACAGGAAAATTTTGGGGCCAAATGA

ACCTGGAGAATTGTATTTTAAAGGCCCGATGAAAATGAAGGGTTATTATAATAAT
```

-continued

```
GAAGAAGCTACTAAAGCAATTATTGATAATGACGGATGGTTGCGCTCTGGTGAT

ATTGCTTATTATGACAATGATGGCCATTTTTATATTGTGGACAGGCTGAAGTCAC

TGATTAAATATAAAGGTTATCAGGTTGCACCTGCTGAAATTGAGGGAATACTCTT

ACAACATCCGTATATTGTTGATGCCGGCGTTACTGGTATACCGGATGAAGCCGCG

GGCGAGCTTCCAGCTGCAGGTGTTGTAGTACAGACTGGAAAATATCTAAACGAA

CAAATCGTACAAGATTATGTTGCCAGTCAAGTTTCAACAGCCAAATGGCTACGTG

GTGGGGTGAAATTTTTGGATGAAATTCCCAAAGGATCAACTGGAAAAATTGACA

GAAAAGTGTTAAGACAAATGTTAGAAAAACACACCAATGGGCATCACCATCACC

ACCATCATCACTAA
```

The invention claimed is:

1. An inhibitor-resistant luciferase comprising enhanced resistance to inhibition by dehydroluciferin and derivatives thereof compared to a luciferase of SEQ ID NO: 3, wherein the inhibitor-resistant luciferase comprises at least 70% sequence identity with SEQ ID NO: 3, and comprises at least one substitution relative to SEQ ID NO: 3 at a position selected from 240, 254, 300, 344, and/or 396 of SEQ ID NO: 3.

2. The inhibitor-resistant luciferase of claim 1, wherein the inhibitor-resistant luciferase exhibits a smaller relative reduction in activity when exposed to dehydroluciferin than a luciferase of SEQ ID NO: 3.

3. The inhibitor-resistant luciferase of claim 1, wherein the inhibitor-resistant luciferase comprises at least one substitution relative to SEQ ID NO: 3, the at least one substitution selected from I240L, Y254S, C300G, T344A, I396K, and/or conservative or semi-conservative variations of such substitutions.

4. The inhibitor-resistant luciferase of claim 1, wherein the inhibitor-resistant luciferase comprises at least 70% sequence identity with SEQ ID NO: 7, and comprises at least one substitution relative to SEQ ID NO: 3, said substitution at a position selected from 240, 254, 344, and/or 396 of SEQ ID NO: 3.

5. A reagent composition comprising the inhibitor-resistant luciferase of claim 1 and a luciferin substrate.

6. The reagent composition of claim 5, further comprising a contaminant comprising a degradation product of luciferin.

7. The reagent composition of claim 6, wherein the contaminant is dehydroluciferin.

8. The reagent composition of claim 5, further comprising magnesium.

9. The reagent composition of claim 5, further comprising one or more additional components selected from the group consisting of: a buffer, a defoamer, an ATPase inhibitor, L-luciferin, aminothiothymidine, an enzyme stabilizer, a detergent, an inhibitor of ATP-generating enzymes, a cell lysing agent, an ATP-extraction agent, co-enzyme A, a thiol reagent, a metal ion chelator, a protease inhibitor, and a salt.

10. The reagent composition of claim 5, wherein the reagent composition is a single liquid reagent.

11. An assay system for detecting or quantifying ATP in a sample, comprising:
(a) a reagent composition of claim 5; and
(b) a sample comprising or suspected of comprising ATP.

12. A method of detecting ATP in a sample comprising: (a) adding to the sample a reagent composition reagent composition of claim 5; and (b) detecting luminescence.

13. The method of claim 12, wherein the sample comprises cells and the method further comprises lysing the cells to generate a cell lysate.

14. A method of quantifying the amount or concentration of ATP in a sample comprising: (a) adding to the sample a reagent composition reagent composition of claim 5; (b) quantifying luminescence from the sample; and (c) comparing the luminescence to a control value to determine the amount or concentration of ATP in the sample.

15. A reagent composition comprising the inhibitor-resistant luciferase of claim 1 and a cationic detergent.

16. The reagent composition of claim 15, wherein the cationic detergent is DTAB (dodecyltrimethylammonium bromide), CTAB (cetyltmethylammonium), Benzalkonium Chloride, or BDDABr (benzyldimethyldodecylammonium bromide).

17. A kit comprising the inhibitor-resistant luciferase of claim 1 and one or more additional components selected from the group consisting of: a buffer, a defoamer, an ATPase inhibitor, an enzyme stabilizer, a detergent, an inhibitor of ATP-generating enzymes, a cell lysing agent, an ATP-extraction agent, co-enzyme A, a thiol reagent, a metal ion chelator, a protease inhibitor, and a salt.

18. A method of detecting luminescence from a luciferin substrate in the presence of ATP and a luciferase inhibitor comprising contacting the luciferin with an inhibitor-resistant luciferase of claim 1.

19. The method of claim 18, wherein the inhibitor is selected from one or more of a dehydroluciferin, an oxyluciferin, and L-luciferin.

* * * * *